(12) United States Patent
Stein et al.

(10) Patent No.: US 11,759,530 B2
(45) Date of Patent: Sep. 19, 2023

(54) TKI PERMEABILITY ENHANCERS

(71) Applicant: City of Hope, Duarte, CA (US)

(72) Inventors: Cy Aaron Stein, Pasadena, CA (US); Daniela Castanotto, Pasadena, CA (US); David Horne, Altadena, CA (US)

(73) Assignee: City of Hope, Duarte, CA (US)

( * ) Notice: Subject to any disclaimer, the term of this patent is extended or adjusted under 35 U.S.C. 154(b) by 109 days.

(21) Appl. No.: 15/527,685

(22) PCT Filed: Nov. 17, 2015

(86) PCT No.: PCT/US2015/061158
§ 371 (c)(1),
(2) Date: May 17, 2017

(87) PCT Pub. No.: WO2016/081503
PCT Pub. Date: May 26, 2016

(65) Prior Publication Data
US 2019/0083650 A1    Mar. 21, 2019

Related U.S. Application Data

(60) Provisional application No. 62/080,863, filed on Nov. 17, 2014.

(51) Int. Cl.
| | | |
|---|---|---|
| A61K 48/00 | (2006.01) |
| A61K 31/10 | (2006.01) |
| A61K 31/352 | (2006.01) |
| A61K 31/404 | (2006.01) |
| A61K 31/4155 | (2006.01) |
| A61K 31/4439 | (2006.01) |
| A61K 31/4709 | (2006.01) |
| A61K 31/52 | (2006.01) |
| A61K 31/55 | (2006.01) |
| A61K 31/7105 | (2006.01) |
| A61K 31/711 | (2006.01) |
| A61K 31/713 | (2006.01) |
| C12N 15/11 | (2006.01) |
| C12N 15/85 | (2006.01) |
| A61K 38/00 | (2006.01) |
| A61P 35/00 | (2006.01) |
| C12N 15/87 | (2006.01) |
| A61K 45/06 | (2006.01) |

(52) U.S. Cl.
CPC ............ *A61K 48/005* (2013.01); *A61K 31/10* (2013.01); *A61K 31/352* (2013.01); *A61K 31/404* (2013.01); *A61K 31/4155* (2013.01); *A61K 31/4439* (2013.01); *A61K 31/4709* (2013.01); *A61K 31/52* (2013.01); *A61K 31/55* (2013.01); *A61K 31/711* (2013.01); *A61K 31/713* (2013.01); *A61K 31/7105* (2013.01); *A61K 38/005* (2013.01); *A61K 45/06* (2013.01); *A61P 35/00* (2018.01); *C12N 15/111* (2013.01); *C12N 15/85* (2013.01); *C12N 15/87* (2013.01); *C12N 2320/32* (2013.01)

(58) Field of Classification Search
CPC .... A61K 48/005; A61K 31/10; A61K 31/352; A61K 31/404; A61K 31/4155; A61K 31/4439; A61K 31/4709; A61K 31/52; A61K 31/55; A61K 31/7105; A61K 31/711; A61K 31/713; A61K 38/005; A61K 45/06; A61P 35/00; C12N 15/111; C12N 15/85; C12N 15/87; C12N 2320/32
See application file for complete search history.

(56) References Cited

U.S. PATENT DOCUMENTS

| | | | |
|---|---|---|---|
| 2006/0030042 A1* | 2/2006 | Brivanlou | C12N 5/0606 435/366 |
| 2009/0304663 A1 | 12/2009 | Kypta | |
| 2011/0178153 A1 | 7/2011 | Chen | |
| 2012/0027873 A1* | 2/2012 | Schlingensiepen | A61K 31/7088 424/649 |
| 2014/0127231 A1* | 5/2014 | Teuscher | A61K 31/7105 424/158.1 |
| 2014/0288178 A1 | 9/2014 | Aifantis et al. | |

FOREIGN PATENT DOCUMENTS

WO    WO-2013173512 A2 *    11/2013    ........... C07K 14/005

OTHER PUBLICATIONS

Rehman et al., Protein kinase A inhibition modulates the intracellular routing of gene delivery vehicles in HeLa cells, leading to productive transfection. Journal of Controlled Release 156 (2011) 76-84. (Year: 2011).*
Enslen et al., Selective activation of p38 mitogen-activated protein (MAP) kinase isoforms by the MAP kinase kinases MKK3 and MKK6. J Biol Chem. Jan. 16, 1998;273(3):1741-8. (Year: 1998).*
Compagno et al., SIRNA-Directed In Vivo Silencing of Androgen Receptor Inhibits the Growth of Castration-Resistant Prostate Carcinomas. PLoS One. 2007; 2(10): e1006 (Year: 2007).*

(Continued)

*Primary Examiner* — Arthur S Leonard
*Assistant Examiner* — Jianjian Zhu
(74) *Attorney, Agent, or Firm* — Mintz, Levin, Cohn, Ferris, Glovsky and Popeo, P.C.

(57) ABSTRACT

Provided herein are, inter alia, methods useful for delivering nucleic acids and kinase inhibitors to a cell. The methods provided herein include the delivery of therapeutic nucleic acids to cancer cells by contacting a cancer cell with a kinase inhibitor and a therapeutic nucleic acid. The methods provided herein are therefore, inter alia, useful for the treatment of cancer.

5 Claims, 10 Drawing Sheets
Specification includes a Sequence Listing.

(56) References Cited

OTHER PUBLICATIONS

Liu et al., 6-Bromoindirubin-3'-oxime inhibits JAK/STAT3 signaling and induces apoptosis of human melanoma cells. Cancer Res. Jun. 1, 2011; 71(11): 3972-3979 (Year: 2011).*

Zhang et al., Reduced Expression of the Androgen Receptor by Third Generation of Antisense Shows Antitumor Activity in Models of Prostate Cancer. Mol Cancer Ther 2011;10:2309-2319 (Year: 2011).*

O'Grady et al., BMC Cancer 2005, 5:125 (Year: 2005).*

International Search Report dated Feb. 5, 2016, for PCT Application No. PCT/US2015/061158, filed Nov. 17, 2015, 4 pages.

Meijer, L. et al. (Dec. 2003). "GSK-3-Selective Inhibitors Derived from Tyrian Purple Indirubins," *Chemistry & Biology* 10(12):1255-1266.

Written Opinion dated Feb. 5, 2016, for PCT Application No. PCT/US2015/061158, filed Nov. 17, 2015, 6 pages.

* cited by examiner

```
                              SEQUENCE LISTING

<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 1
tcagtctgat aagcta                                                        16

<210> SEQ ID NO 2
<211> LENGTH: 22
<212> TYPE: RNA
<213> ORGANISM: Artificial sequence
<220> FEATURE:
<223> OTHER INFORMATION: Synthetic polynucleotide

<400> SEQUENCE: 2
uagcuuauca gacugauguu ga                                                 22

<210> SEQ ID NO 3
<211> LENGTH: 16
<212> TYPE: DNA
<213> ORGANISM: Artificial Sequence
<220> FEATURE:
<223> OTHER INFORMATION: Syntheitc polynucleotide
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(1)
<223> OTHER INFORMATION: Backbone modified with phosphorothioate
<220> FEATURE:
<221> NAME/KEY: misc_feature
<222> LOCATION: (2)..(2)
<223> OTHER INFORMATION: Backbone modified with phosphorothioate
<220> FEATURE:
<221> NAME/KEY: misc_feature
<222> LOCATION: (3)..(3)
<223> OTHER INFORMATION: Backbone modified with phosphorothioate
<220> FEATURE:
<221> NAME/KEY: misc_feature
<222> LOCATION: (4)..(4)
<223> OTHER INFORMATION: Backbone modified with phosphorothioate
<220> FEATURE:
<221> NAME/KEY: misc_feature
<222> LOCATION: (5)..(5)
<223> OTHER INFORMATION: Backbone modified with phosphorothioate
<220> FEATURE:
<221> NAME/KEY: misc_feature
<222> LOCATION: (6)..(6)
<223> OTHER INFORMATION: Backbone modified with phosphorothioate
<220> FEATURE:
<221> NAME/KEY: misc_feature
<222> LOCATION: (7)..(7)
<223> OTHER INFORMATION: Backbone modified with phosphorothioate
<220> FEATURE:
<221> NAME/KEY: misc_feature
<222> LOCATION: (8)..(8)
<223> OTHER INFORMATION: Backbone modified with phosphorothioate
<220> FEATURE:
<221> NAME/KEY: misc_feature
<222> LOCATION: (9)..(9)
```

```
<223> OTHER INFORMATION: Backbone modified with phosphorothioate
<220> FEATURE:
<221> NAME/KEY: misc_feature
<222> LOCATION: (10)..(10)
<223> OTHER INFORMATION: Backbone modified with phosphorothioate
<220> FEATURE:
<221> NAME/KEY: misc_feature
<222> LOCATION: (11)..(11)
<223> OTHER INFORMATION: Backbone modified with phosphorothioate
<220> FEATURE:
<221> NAME/KEY: misc_feature
<222> LOCATION: (12)..(12)
<223> OTHER INFORMATION: Backbone modified with phosphorothioate
<220> FEATURE:
<221> NAME/KEY: misc_feature
<222> LOCATION: (13)..(13)
<223> OTHER INFORMATION: Backbone modified with phosphorothioate
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (14)..(14)
<223> OTHER INFORMATION: Backbone modified with phosphorothioate
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (15)..(15)
<223> OTHER INFORMATION: Backbone modified with phosphorothioate

<400> SEQUENCE: 3
ctcccaacgt gcgcca                                              16

<210> SEQ ID NO 4
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 4
accaagtttc ttcagc                                              16

<210> SEQ ID NO 5
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 5
ctcccaacgt gcgcca                                              16
```

TKI PERMEABILITY ENHANCERS

CROSS-REFERENCE TO RELATED APPLICATIONS

This application is a national stage entry under 35 U.S.C. 371 of International Application No. PCT/US2015/061158, filed Nov. 17, 2015, which claims the benefit of U.S. Provisional Application No. 62/080,863, filed Nov. 17, 2014, which are hereby incorporated by reference in their entirety and for all purposes.

SEQUENCE LISTING

The Sequence Listing written in file 048440-552001WO_ST25.txt, created on Dec. 6, 2015, 2.87 kilobytes, machine format IBM-PC, MS-Windows operating system, is hereby incorporated by reference.

BACKGROUND OF THE INVENTION

Treatment of cancer using anticancer nucleic acids (e.g., miRNAs) can be hampered by limited penetration of the nucleic acid molecules into the deeper layers of the tumor tissue. The low amounts of therapeutic nucleic acid molecules being delivered to cancer cells impacts treatment efficacy significantly. The methods and compositions provided herein address these and other problems in the art. The methods provided herein include contacting a cell (e.g., a cancer cell forming part of a tumor) with a nucleic acid (e.g., an anticancer nucleic acid) and a kinase inhibitor. Surprisingly, the penetration of the nucleic acids increases in the presence of the kinase inhibitor and the nucleic acid may be delivered to cells deep within a tumor.

BRIEF SUMMARY OF THE INVENTION

In one aspect, a method of delivering a nucleic acid to a cell is provided. The method includes (i) contacting a cell with a nucleic acid and a kinase inhibitor selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor and (ii) allowing the nucleic acid to enter the cell.

In another aspect, a pharmaceutical formulation is provided. The pharmaceutical formulation includes a pharmaceutically acceptable excipient, a therapeutic nucleic acid and a kinase inhibitor selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor.

In another aspect, a method of treating cancer in a subject in need thereof is provided. The method includes administering to the subject an anti-cancer nucleic acid and a kinase inhibitor in a combined effective amount. The kinase inhibitor is selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor.

BRIEF DESCRIPTION OF THE DRAWINGS

FIG. 1: Fluorescence imaging of anti-mir21-ASO (antisense oligonucleotide; SEQ ID NO:1) 6 days after treatment of HCT116-GFPmiR21 cells (Castanotto et al., 2007 *Nucleic Acids Res.* 35:5154-5164) with: Panel A. No drug. Panel B. GSK-3β-inhibitor (6-BIO) 1 μM having the structure of:

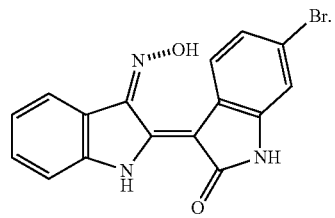

Panel C. Repeat GSK-3β-inhibitor (6-BIO) 1 μM. Panel D. Imatinib 1 μM. Panel E. XNH-2s present at 0.1 μM having the structure:

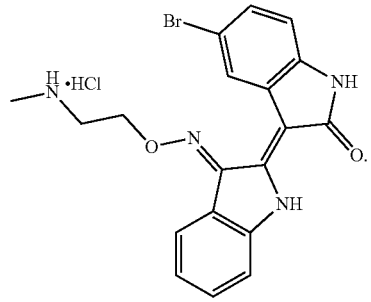 [SMILES: CNCCO/N=C1/C(=C2/C(=O)Nc3ccc(Br)cc32)Nc2ccccc21 ; Cl]

Panel F. XNH-8 present at 0.1 μM having the structure:

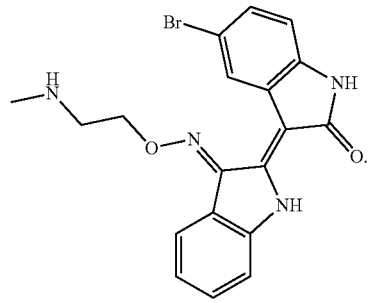 [SMILES: CNCCO/N=C1/C(=C2/C(=O)Nc3ccc(Br)cc32)Nc2ccccc21]

Figure 1:
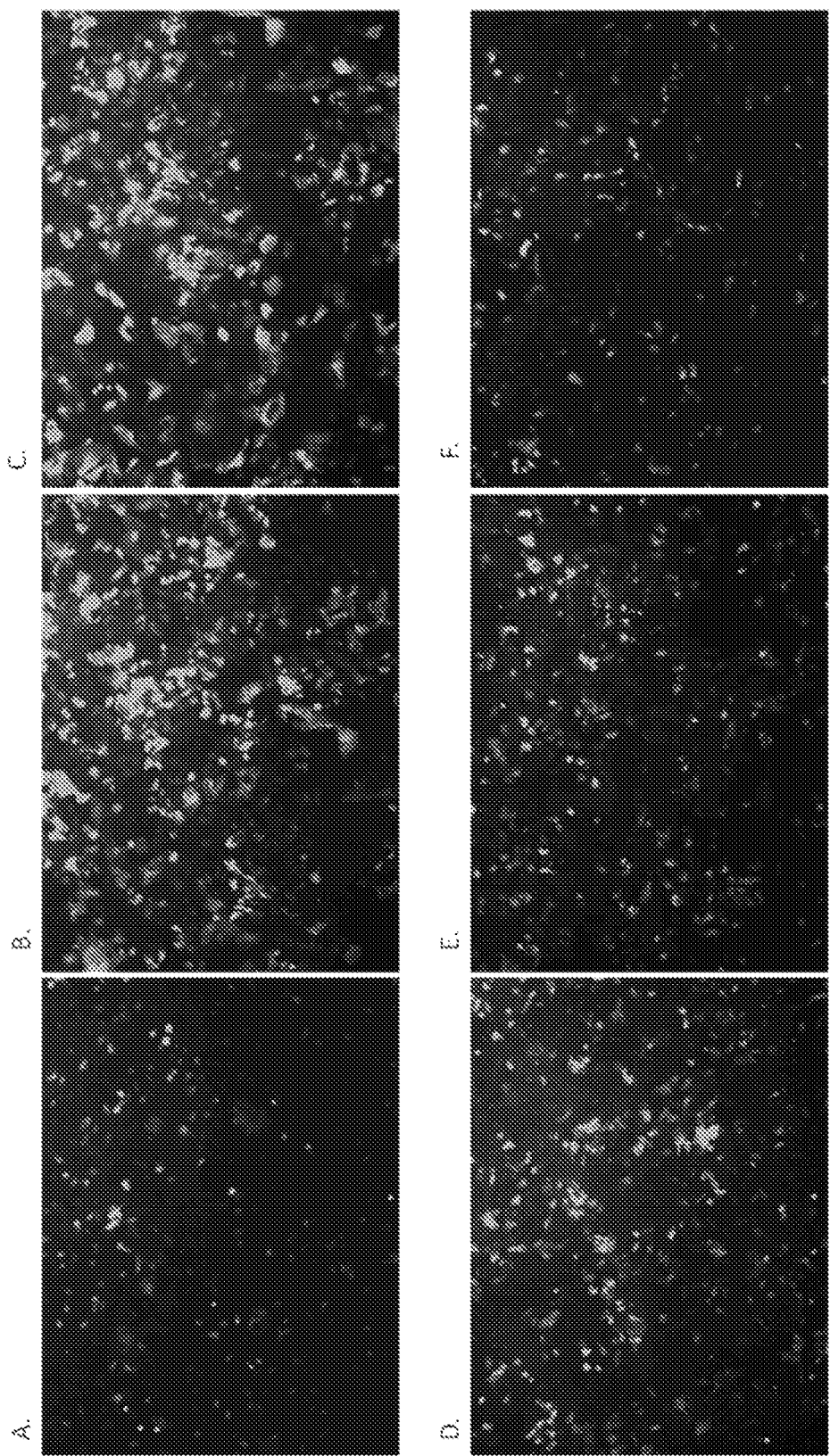
Figure 2:
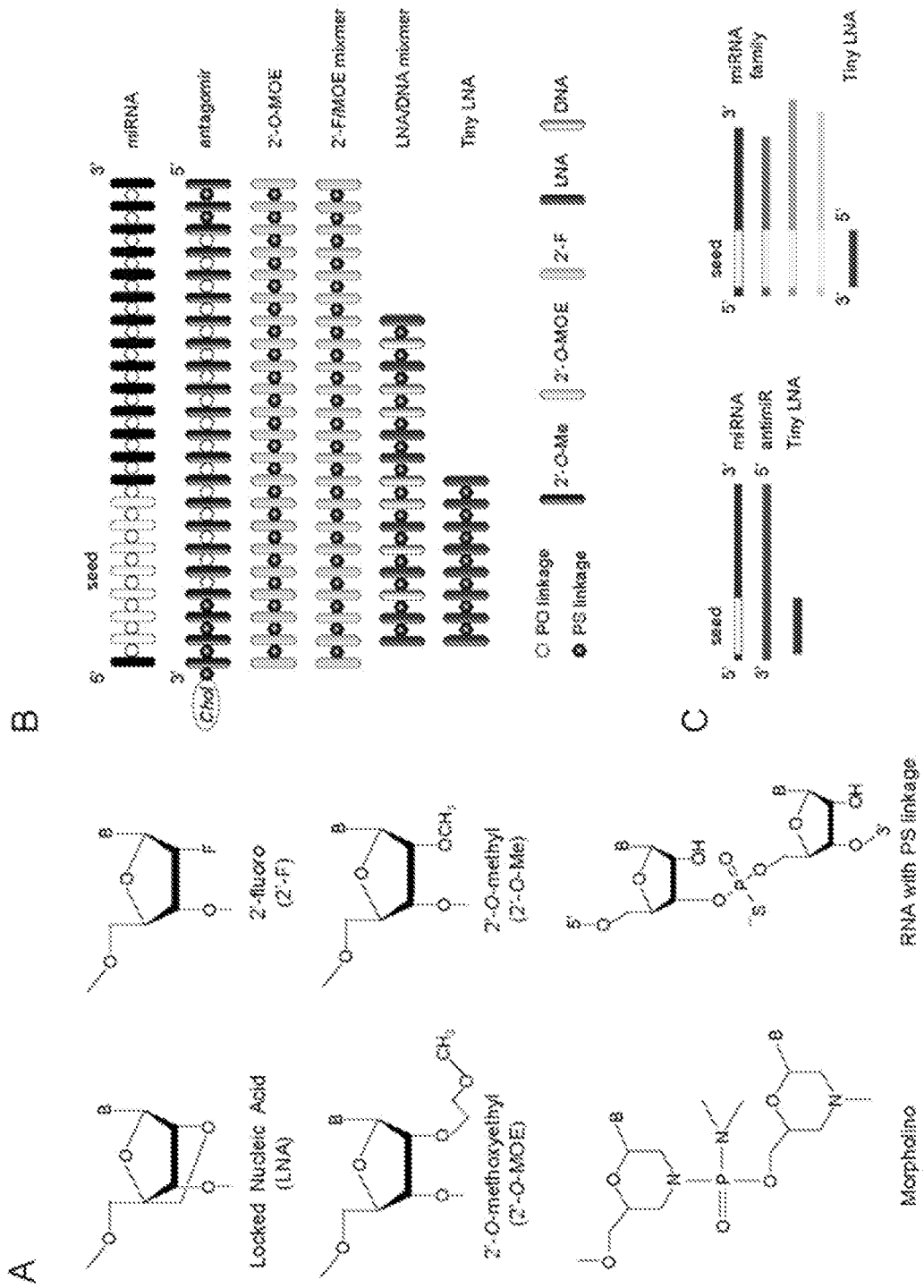

FIG. 2: Chemically modified oligonucleotides. Panel A. Schematic of modified nucleotide base. Panels B. and C. Schematic of modified oligonucleotide sequences.

Figure 3:
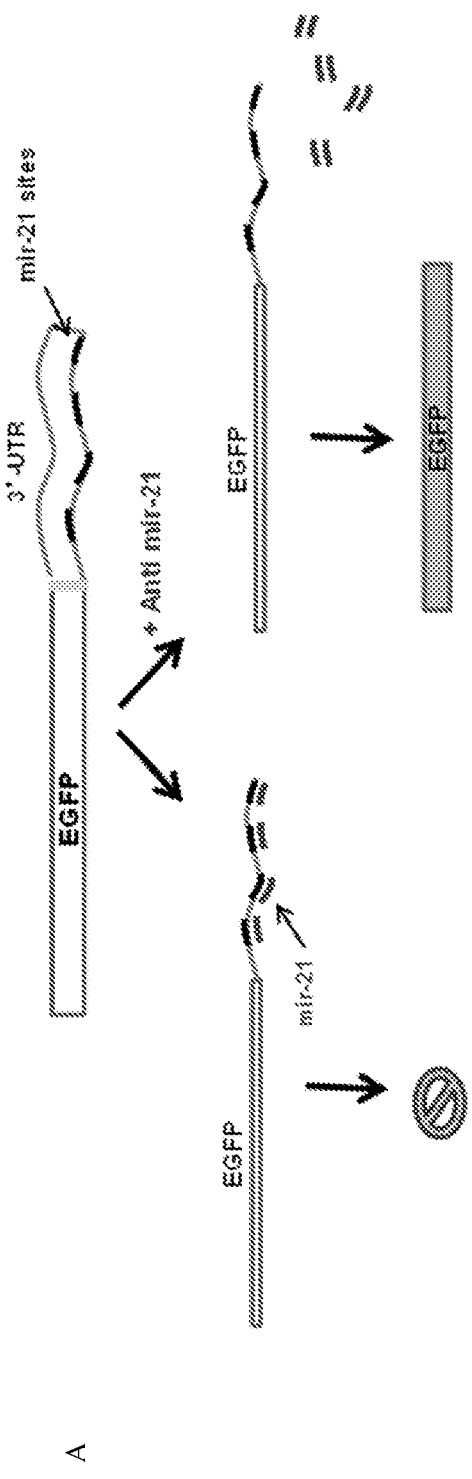

FIG. 3: Large Scale Drug Screen (evaluation of 80.000 compounds). Panel A. Schematic of eGFP activation. Panel B. Basal level of activation (anti-mir21). Panel C. Decreased uptake (anti-mir21+sorafenib). Panel D. Increased uptake (anti-mir21+imatinib). Panel E. Anti-mir21 pretreatment and increased release (anti-mir21+imatinib).

Figure 4:
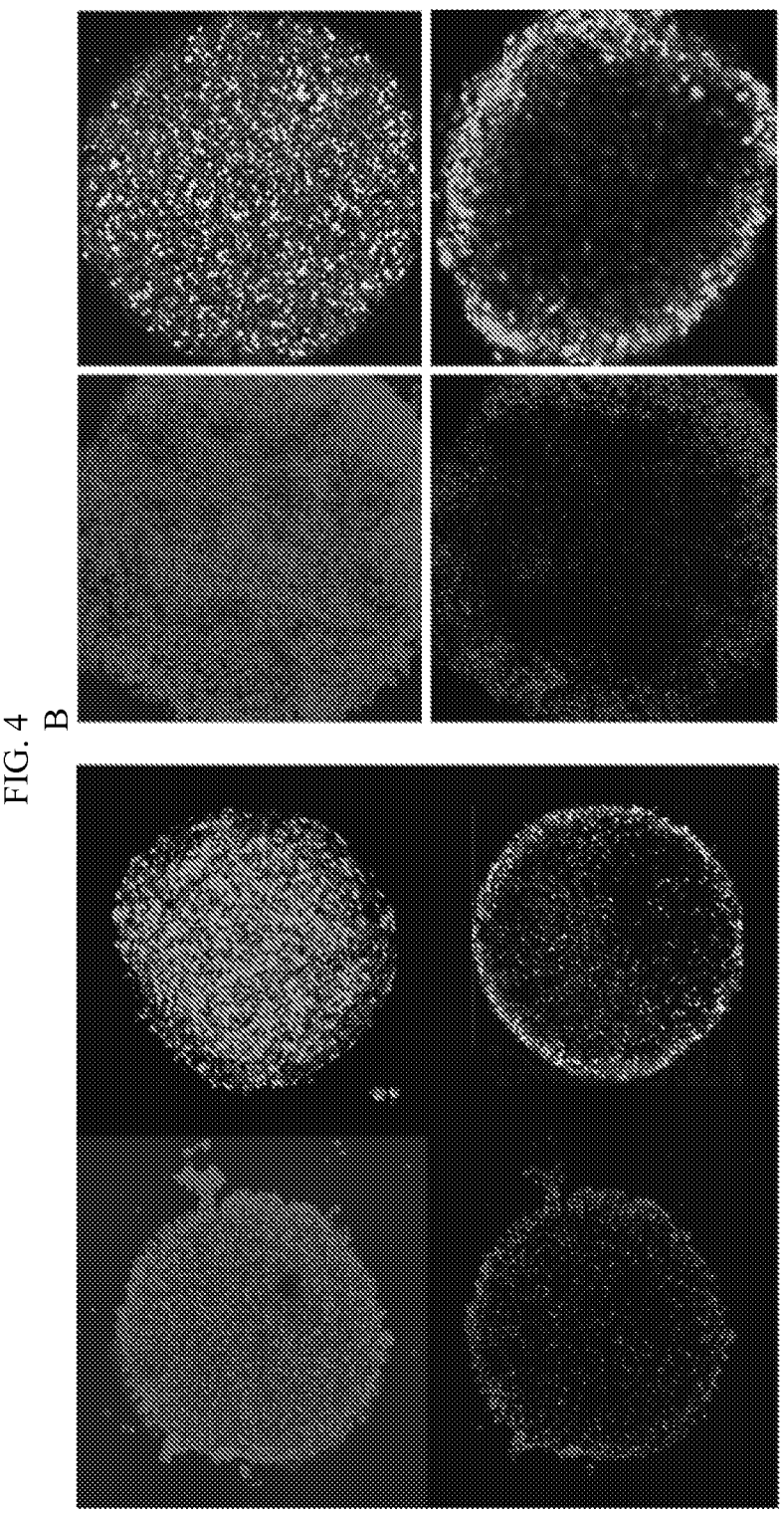

FIG. 4: LNA (Locked Nucleic Acid)-ASO cannot effectively penetrate tumor spheroids. Confocal images of Z-stacks top (top images of panels A and B) to middle sections (bottom images of panels A and B) are shown in two magnifications (left panel images taken at lower magnification; right panel images taken at higher magnification). In panels A and B: left top and left bottom image shows ASO expression; right top and right bottom image shows eGFP expression.

Figure 5:
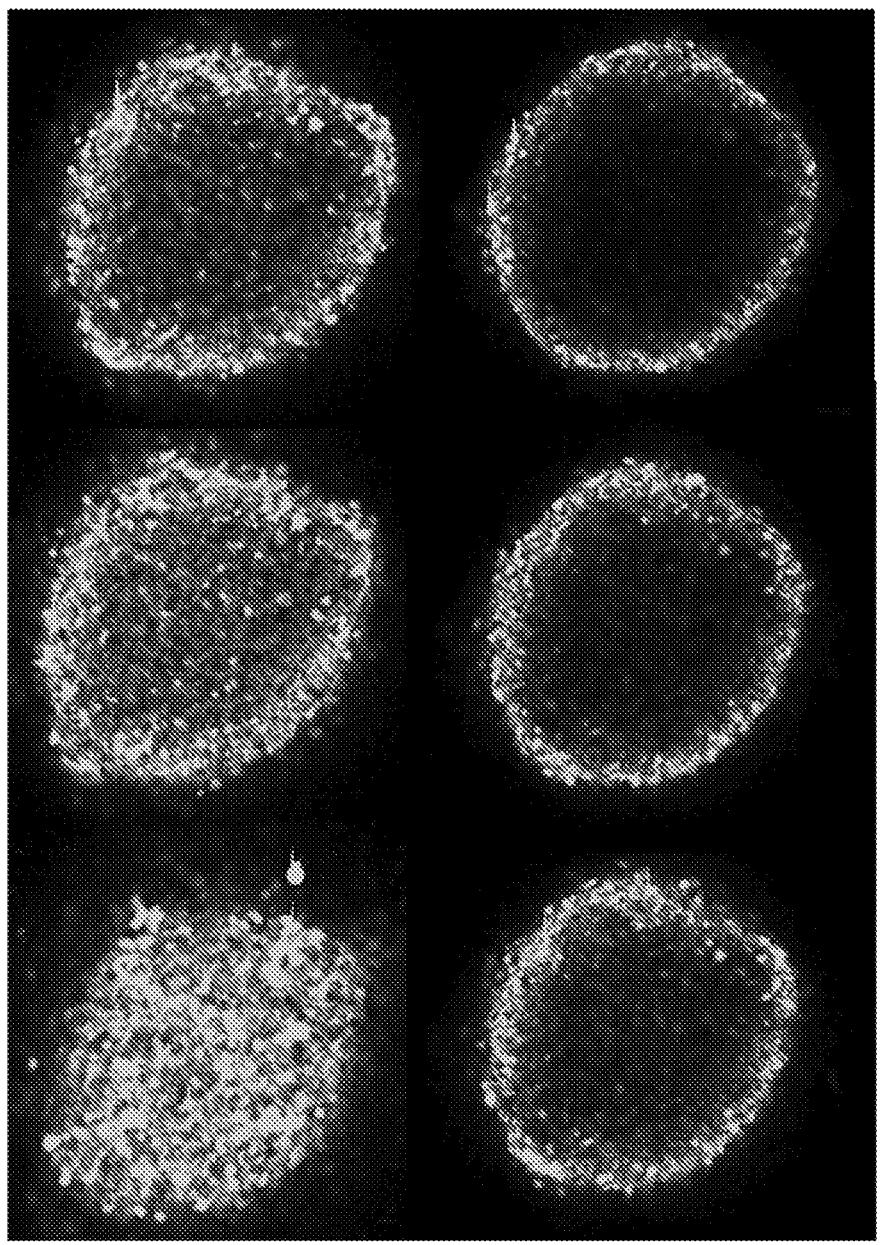

FIG. 5: LNA (Locked Nucleic Acid)-ASO cannot effectively penetrate tumor spheroids. "Slicing" the tumor spheroids shows that only a few layers of the cells can functionally uptake the LNA-ASO. Confocal images of a tumor spheroid are shown as Z-stack from left to right, and top to bottom).

Figure 6:
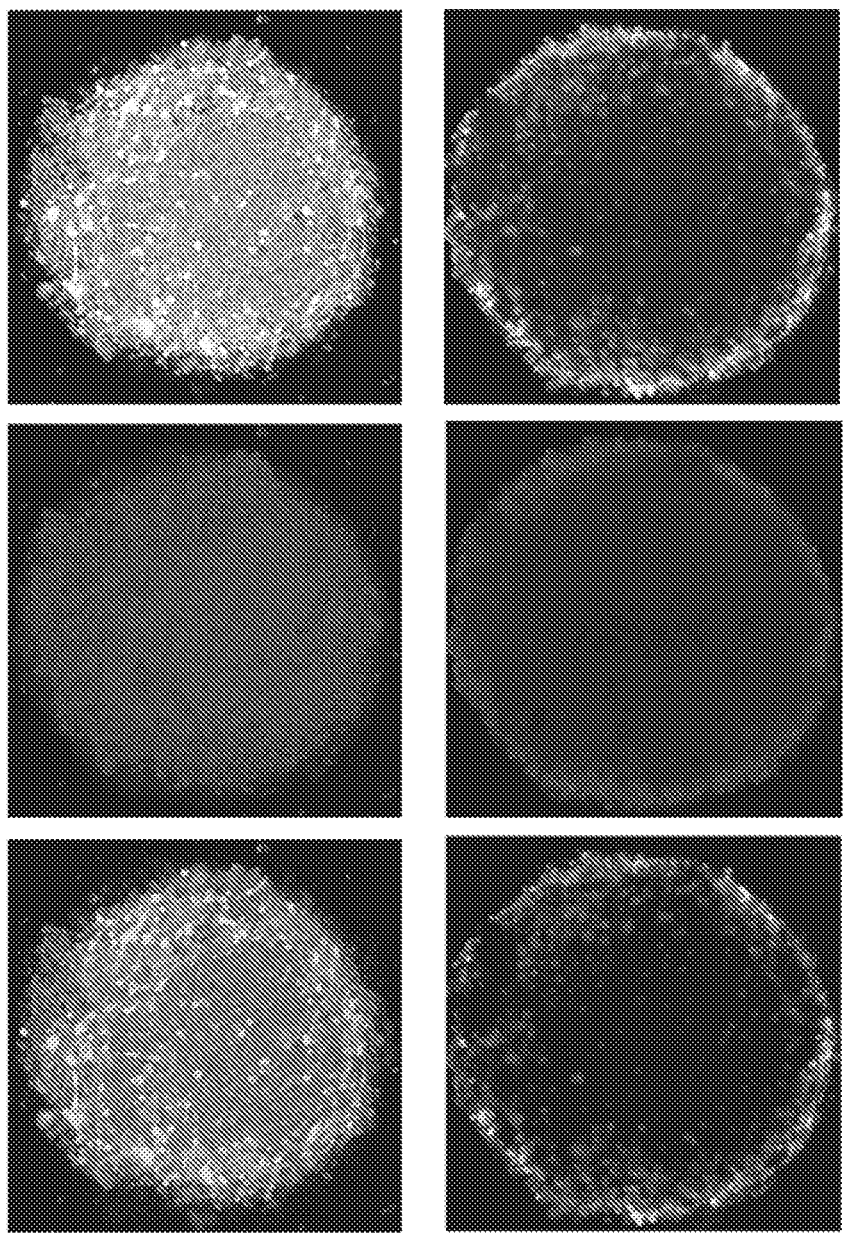

FIG. 6: Doxorubicin shows more uniform penetration into the tumor spheroids. Upper panel shows top sections of spheroid, lower panel shows middle section of spheroid. Left images top and bottom show expression of eGFP. Middle images top and bottom show expression of ASO. Right images top and bottom show co-expression of eGFP and ASO. Confocal images of Z-stack: top and middle sections.

Figure 7:
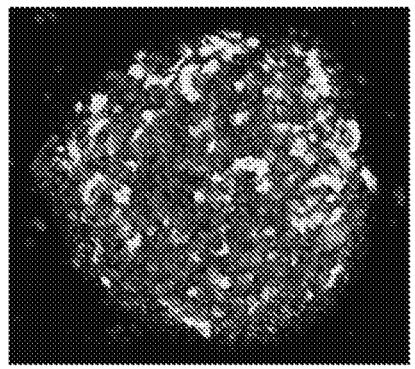
Figure 7:
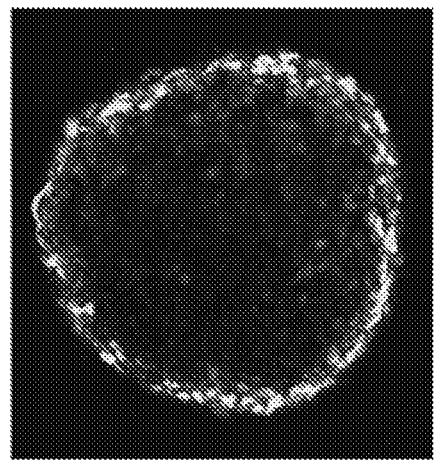
Figure 7:
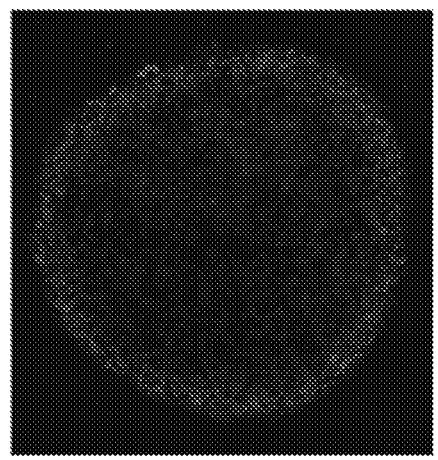
Figure 7:
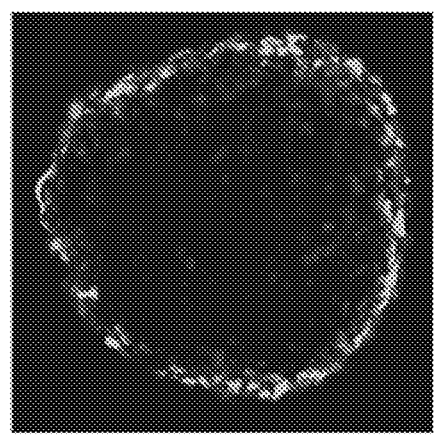

FIG. 7: Penetration into the tumor spheroids in the presence of sorafenib. Top image shows top section of spheroid with cells co-expressing ASO and eGFP. Lower panel shows images of middle section of spheroid with cells expressing eGFP (bottom left image), ASO (bottom middle image) and cells co-expressing eGFP and ASO (bottom right image). Confocal images of Z-stack: top and middle sections.

Figure 8:
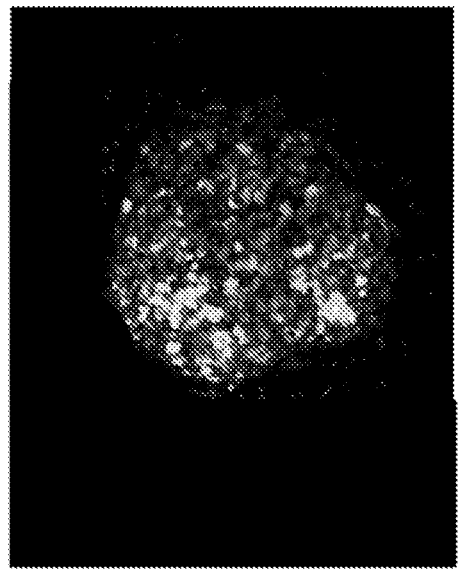
Figure 8:
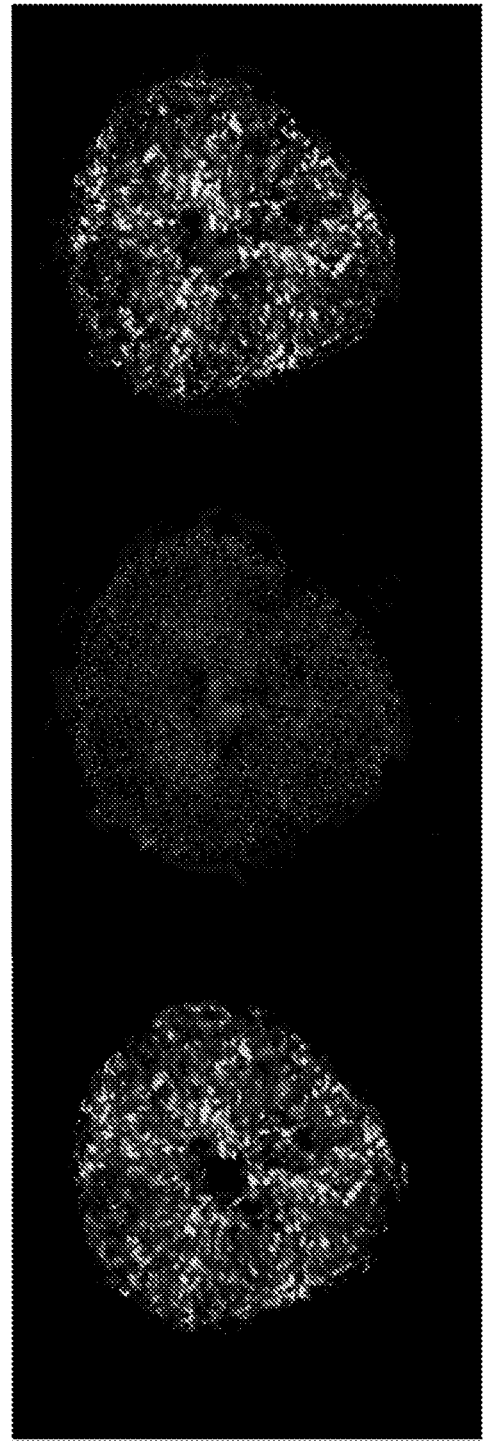

FIG. 8: Penetration into the tumor spheroids in the presence of imatinib. Top image shows top section of spheroid with cells co-expressing ASO and eGFP. Lower panel shows images of middle section of spheroid with cells expressing eGFP (bottom left image), ASO (bottom middle image) and cells co-expressing eGFP and ASO (bottom right image). Confocal images of Z-stack: top and middle sections.

Figure 9:
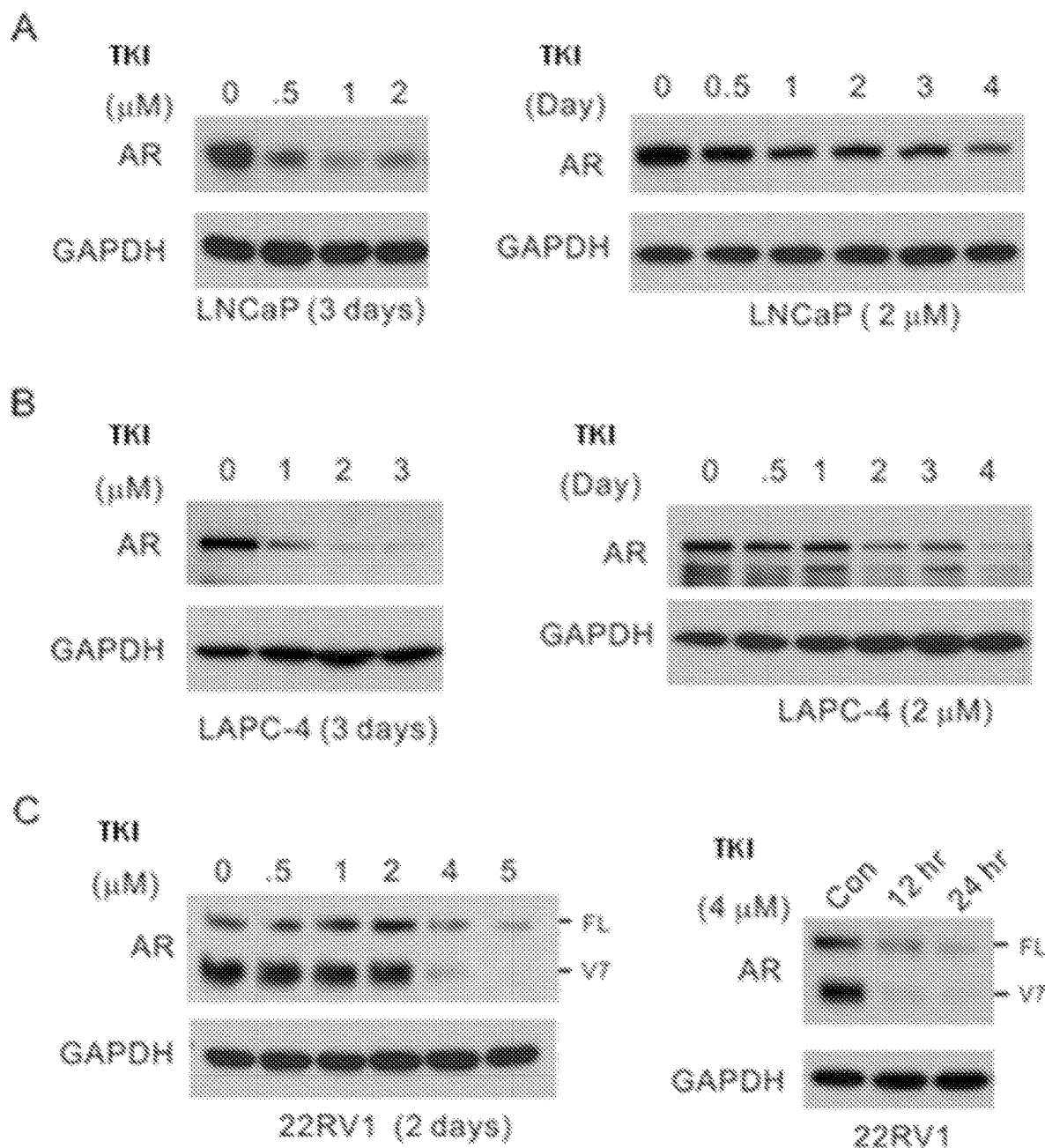

FIG. 9: A TKI inhibitor (6-BIO) downregulates the androgen receptor in prostate cancer cells. Panels A-C, Prostate cancer cell lines LNCaP (A), LAPC-4 (B), and 22RV1 (C) were treated with inhibitor at indicated concentrations for indicated incubation times. FL, AR full length; V7, AR variant 7.

Figure 10:
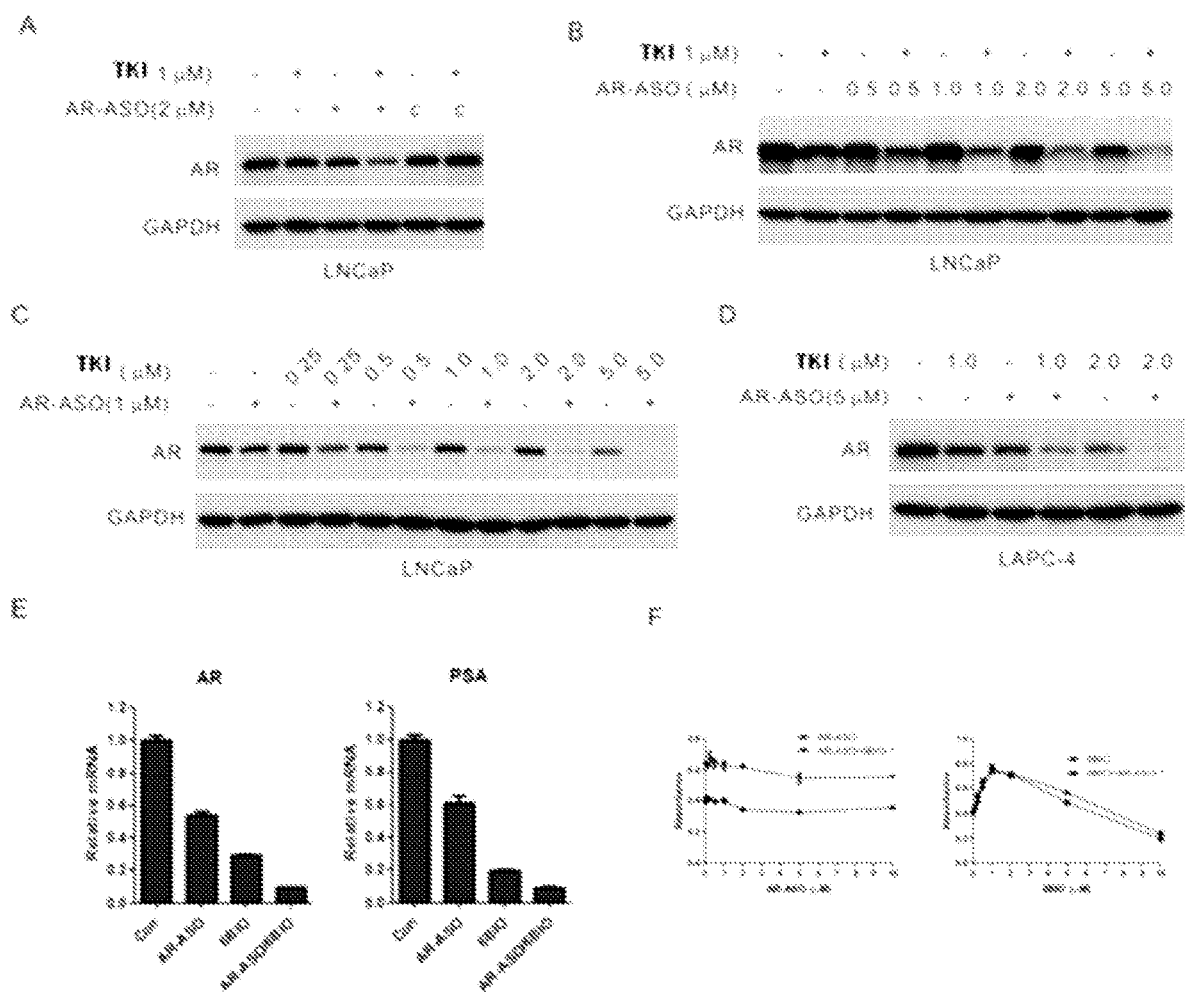

FIG. 10: TKI synergizes AR-ASO against AR expression and the AR signal pathway. Panels A-D, LNCaP (A, B and C) and LAPC-4 cells (D) were treated with TKI inhibitor (6-BIO) and AR-ASO at the indicated concentrations for 2 days. Panel E. RT-PCR assay of LNCaP cells treated with 1 uM TKI inhibitor (6-BIO) and 1 uM AR-ASO for 2 days. Panel F. The combination of TKI and AR-ASO did not show increased cytoxicity in LNCaP cells. MTS assay of LNCaP treated for 3 days with 1 uM TKI or 1 uM AR-ASO (AR-ASO-1) in the presence of the titrations of the paired drug.

DETAILED DESCRIPTION OF THE INVENTION

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligonucleotides or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiesters, phosphodiester derivatives, or a combination of both.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

The term "aptamer" as provided herein refers to oligonucleotides (e.g. short oligonucleotides or deoxyribonucleotides), that bind (e.g. with high affinity and specificity) to proteins, peptides, and small molecules. Aptamers may have secondary or tertiary structure and, thus, may be able to fold into diverse and intricate molecular structures. Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino acid side chains to expand the aptamer's chemical diversity. As a result high affinity aptamers for almost any protein target are enriched and identified. Aptamers exhibit many desirable properties for targeted drug delivery, such as ease of selection and synthesis, high binding affinity and specificity, low immunogenicity, and versatile synthetic accessibility. To date, a variety of anti-cancer agents (e.g. chemotherapy drugs, toxins, and siRNAs) have been successfully delivered to cancer cells in vitro using apatmers.

An "antisense nucleic acid" as referred to herein is a nucleic acid (e.g. DNA or RNA molecule) that is complementary to at least a portion of a specific target nucleic acid (e.g. an mRNA translatable into a protein such as for example, Bcl-2, androgen receptor) and is capable of reducing transcription of the target nucleic acid (e.g. mRNA from DNA) or reducing the translation of the target nucleic acid (e.g. mRNA) or altering transcript splicing (e.g. single stranded morpholino oligonucleotide). See, e.g., Weintraub, *Scientific American*, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbone modified nucleotides.

In the cell, the antisense nucleic acids hybridize to the corresponding mRNA, forming a double-stranded molecule. The antisense nucleic acids interfere with the translation of the mRNA, since the cell will not translate an mRNA that is double-stranded. The use of antisense methods to inhibit the in vitro translation of genes is well known in the art (Marcus-Sakura, *Anal. Biochem.*, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or precursors, such as nucleotide analogs), morpholinos (morpholino oligomers, morpholino oligonucleotide), short hairpin RNAs (shRNA), micro RNAs (miRNA), saRNAs (small activating RNAs) and small nucleolar RNAs (snoRNA) or certain of their derivatives or precursors.

A "siRNA," "small interfering RNA," "small RNA," or "RNAi" as provided herein, refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a siRNA or RNAi is a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

A "saRNA," or "small activating RNA" as provided herein refers to a nucleic acid that forms a double stranded RNA, which double stranded RNA has the ability to increase or activate expression of a gene or target gene when expressed in the same cell as the gene or target gene. The complementary portions of the nucleic acid that hybridize to form the double stranded molecule typically have substantial or complete identity. In one embodiment, a saRNA is a nucleic acid that has substantial or complete identity to a target gene and forms a double stranded saRNA. Typically, the nucleic acid is at least about 15-50 nucleotides in length (e.g., each complementary sequence of the double stranded saRNA is 15-50 nucleotides in length, and the double stranded saRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), or adrenocortical suppressant (e.g., mitotane, aminoglutethimide), epipodophyllotoxins (e.g., etoposide).

Further examples of anti-cancer agents include, but are not limited to, antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Disease" or "condition" refer to a state of being or health status of a patient or subject capable of being treated with a compound, pharmaceutical composition, or method provided herein. In embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma).

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g., non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma *villosum*.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) or viral disease (e.g., HIV infection associated disease)) is caused by (in whole or in part), or a symptom of the disease is caused by (in whole or in part) the substance or substance activity or function.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a nucleic acid as described herein and a cell (e.g., cancer cell).

As defined herein, the term "inhibition", "inhibit", "inhibiting" and the like in reference to kinase-inhibitor interaction means negatively affecting (e.g., decreasing) the activity or function of the protein (kinase) (e.g. decreasing gene transcription or translation) relative to the activity or function of the protein (e.g. kinase) in the absence of the inhibitor. In embodiments, inhibition refers to reduction of a disease or symptoms of disease (e.g., cancer). In embodiments, inhibition refers to a reduction in the activity of a signal transduction pathway or signaling pathway (e.g. reduction of a kinase signaling pathway). Thus, inhibition includes, at least in part, partially or totally blocking stimulation, decreasing, preventing, or delaying activation, or inactivating, desensitizing, or down-regulating transcription, translation, signal transduction or enzymatic activity or the amount of a protein (e.g. a kinase). In embodiments, inhibition refers to inhibition of Abl kinase, p38 mitogen-activated protein (p38 MAP) kinase, glycogen synthase kinase (GSK), inositol 1,4,5-trisphosphate 3 kinase (IP3-K), activin receptor-like kinase (ALK), myosin light chain kinase (MLCK), proto-oncogene serine/threonine-protein 1 (PIM1) kinase, phosphatidylinositol-4,5-bisphosphate 3 (PI3) kinase, rho-associated protein kinase (ROCK), or transforming growth factor beta receptor (TGFβ Receptor) kinase.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a compound or small molecule that inhibits a kinase (e.g., tyrosine kinase) e.g., by binding, partially or totally blocking stimulation, decrease, prevent, or delay activation, or inactivate, desensitize, or downregulate signal transduction, gene expression or enzymatic activity necessary for protein activity. Inhibition as provided herein may also include decreasing or blocking a kinase activity (e.g., tyrosine phosphorylation) by expressing a mutant form of said kinase thereby decreasing or blocking its activity.

For specific kinases described herein (e.g., p38 MAP kinase), the named kinase includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the kinase is the protein as identified by its NCBI sequence reference. In other embodiments, the kinase is the protein as identified by its NCBI sequence reference, homolog or functional fragment thereof.

Methods of Delivering Nucleic Acids

Provided herein are, inter alia, methods for delivering nucleic acids to a cell. In the methods provided a cell may be contacted with a nucleic acid (e.g., a therapeutic nucleic acid) and a kinase inhibitor, thereby allowing the nucleic acid to enter the cell. Thus, in one aspect, a method of delivering a nucleic acid to a cell is provided. The method includes (i) contacting a cell with a nucleic acid and a kinase inhibitor selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor and (ii) allowing the nucleic acid to enter the cell. In embodiments, the kinase inhibitor is an Abl kinase inhibitor, a p38α MAP kinase inhibitor, a GSK-3α inhibitor, a GSK-3β inhibitor, a IP3-K inhibitor, an ALK 4 inhibitor, an ALK 5 inhibitor, an MLCK 2 inhibitor, an PIM1 kinase inhibitor, an PI3α kinase inhibitor, a ROCK-II inhibitor or a TGFβ Receptor I kinase inhibitor.

In embodiments, the kinase inhibitor is an Abl kinase inhibitor. An Abl kinase inhibitor as referred to herein is a kinase inhibitor capable of inhibiting an Abl kinase. An "Abl kinase" as referred to herein includes any of the Abelson murine leukemia viral oncogene homolog 1 (Abl 1) tyrosine kinase naturally occurring forms, homologs or variants that maintain the activity of Abl kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the Abl kinase is the protein as identified by the NCBI sequence reference GI:62362414. In embodiments, the Abl kinase is the protein as identified by the NCBI sequence reference GI:62362414, homolog or functional fragment thereof.

In embodiments, the kinase inhibitor is a p38 MAP kinase inhibitor. A p38 MAP kinase inhibitor as referred to herein is a kinase inhibitor capable of inhibiting a p38 MAP kinase. A "p38 MAP kinase" as referred to herein includes any of the p38 mitogen-activated protein (MAP) kinases naturally occurring forms, homologs or variants that maintain the activity of p38 MAP kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the p38 MAP kinase is the protein as identified by the NCBI sequence reference GI:20128774. In embodiments, the p38 MAP kinase is the protein as identified by the NCBI sequence reference GI:20128774, homolog or functional fragment thereof. In embodiments, the p38 MAP kinase is the protein as identified by the NCBI sequence reference GI:48255970. In embodiments, the p38 MAP kinase is the protein as identified by the NCBI sequence reference GI:48255970, homolog or functional fragment thereof. In embodiments, the p38 MAP kinase is the protein as identified by the NCBI sequence reference GI:4506085. In embodiments, the p38 MAP kinase is the protein as identified by the NCBI sequence reference GI:4506085, homolog or functional fragment thereof. In embodiments, the p38 MAP kinase is the protein as identified by the NCBI sequence reference GI:4503069. In embodiments, the p38 MAP kinase is the protein as identified by the NCBI sequence reference GI:4503069, homolog or functional fragment thereof.

In embodiments, the kinase inhibitor is a glycogen synthase (GSK) kinase inhibitor. A GSK inhibitor as referred to herein is a kinase inhibitor capable of inhibiting a GSK serine/threonine kinase. A "GSK kinase" as referred to herein includes any of the glycogen synthase (GSK) kinase naturally occurring forms, homologs or variants that maintain the activity of GSK kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the GSK kinase is the protein as identified by the NCBI sequence reference GI:49574532. In embodiments, the GSK kinase is the protein as identified by the NCBI sequence reference GI:49574532, homolog or functional fragment thereof. In embodiments, the GSK kinase is the protein as identified by the NCBI sequence reference GI:225903437. In embodiments, the GSK kinase is the protein as identified by the NCBI sequence reference GI:225903437, homolog or functional fragment thereof.

In embodiments, the kinase inhibitor is an inositol 1, 4, 5-trisphosphate 3 kinase (IP3-K) inhibitor. An IP3-K inhibitor as referred to herein is a kinase inhibitor capable of inhibiting an IP3-K serine/threonine kinase. An "IP3-K kinase" as referred to herein includes any of the IP3-K kinase naturally occurring forms, homologs or variants that maintain the activity of IP3-K kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the IP3-K kinase is the protein as identified by the UniProt sequence reference P23677-1. In embodiments, the IP3-K kinase is the protein as identified by the UniProt sequence reference P23677-1, homolog or functional fragment thereof. In embodiments, the IP3-K kinase is the protein as identified by the UniProt sequence reference P27987-1. In embodiments, the IP3-K kinase is the protein as identified by the UniProt sequence reference P27987-1, homolog or functional fragment thereof.

In embodiments, the kinase inhibitor is an activin receptor-like kinase (ALK) inhibitor. An ALK inhibitor as referred to herein is a kinase inhibitor capable of inhibiting an ALK kinase. An "ALK kinase" as referred to herein includes any of the ALK kinase naturally occurring forms, homologs or variants that maintain the activity of ALK kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the ALK kinase is the protein as identified by the NCBI sequence reference GI: 431035. In embodiments, the ALK kinase is the protein as identified by the NCBI sequence reference GI: 431035, homolog or functional fragment thereof. In embodiments, the ALK kinase is the protein as identified by the NCBI sequence reference GI:298566263. In embodiments, the ALK kinase is the protein as identified by the NCBI sequence reference GI:298566263, homolog or functional fragment thereof. In embodiments, the ALK kinase is the protein as identified by the NCBI sequence reference GI:222831623. In embodiments, the ALK kinase is the protein as identified by the NCBI sequence reference GI:222831623, homolog or functional fragment thereof. In embodiments, the ALK kinase is the protein as identified by the NCBI sequence reference GI:518828582. In embodiments, the ALK kinase is the protein as identified by the NCBI sequence reference GI:518828582, homolog or functional fragment thereof. In embodiments, the ALK kinase is the protein as identified by the NCBI sequence reference GI: 161333836. In embodiments, the ALK kinase is the protein as identified by the NCBI sequence reference GI: 161333836, homolog or functional fragment thereof.

In embodiments, the kinase inhibitor is a myosin light chain kinase (MLCK) inhibitor. An MLCK inhibitor as referred to herein is a kinase inhibitor capable of inhibiting an MLCK serine/threonine kinase. An "MLCK kinase" as referred to herein includes any of the MLCK kinase naturally occurring forms, homologs or variants that maintain the activity of MLCK kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the MLCK kinase is the protein as identified by the NCBI sequence reference GI: 116008192. In embodiments, the MLCK kinase is the protein as identified by the NCBI sequence reference GI: 116008192, homolog or functional fragment thereof. In embodiments, the MLCK kinase is the protein as identified by the NCBI sequence reference GI: 14993776. In embodiments, the MLCK kinase is the protein as identified by the NCBI sequence reference GI: 14993776, homolog or functional fragment thereof.

In embodiments, the kinase inhibitor is a proto-oncogene serine/threonine protein 1 (PIM1) inhibitor. A PIM1 inhibitor as referred to herein is a kinase inhibitor capable of inhibiting a PIM1 serine/threonine kinase. An "PIM1 kinase" as referred to herein includes any of the PIM1 kinase naturally occurring forms, homologs or variants that maintain the activity of PIM1 kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the PIM1 kinase is the protein as identified by the NCBI sequence reference GI:342307046. In embodiments, the PIM1 kinase is the protein as identified by the NCBI sequence reference GI:342307046, homolog or functional fragment thereof.

In embodiments, the kinase inhibitor is a phosphatidylinositol-4,5-bisphosphate 3 (PI3) inhibitor. A PI3 inhibitor as referred to herein is a kinase inhibitor capable of inhibiting a PI3 kinase. An "PI3 kinase" as referred to herein includes any of the PI3 kinase naturally occurring forms, homologs or variants that maintain the activity of PI3 kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the PI3 kinase is the protein as identified by the NCBI sequence reference GI:54792082. In embodiments, the PI3 kinase is the protein as identified by the NCBI sequence reference GI:54792082, homolog or functional fragment thereof.

In embodiments, the kinase inhibitor is a rho-associated protein kinase (ROCK) inhibitor. A ROCK inhibitor as referred to herein is a kinase inhibitor capable of inhibiting a ROCK kinase. An "ROCK kinase" as referred to herein includes any of the ROCK kinase naturally occurring forms, homologs or variants that maintain the activity of ROCK kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the ROCK kinase is the protein as identified by the NCBI sequence reference GI:4885583. In embodiments, the ROCK kinase is the protein as identified by the NCBI sequence reference GI:4885583, homolog or functional fragment thereof. In embodiments, the ROCK kinase is the protein as identified by the UniProt sequence reference O75116-1. In embodiments, the ROCK kinase is the protein as identified by the UniProt sequence reference O75116-1, homolog or functional fragment thereof.

In embodiments, the kinase inhibitor is a transforming growth factor beta receptor (TGFβR) kinase inhibitor. A TGFβR inhibitor as referred to herein is a kinase inhibitor capable of inhibiting a TGFβR kinase. An "TGFβR kinase" as referred to herein includes any of the TGFβR kinase naturally occurring forms, homologs or variants that maintain the activity of TGFβR kinase (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the TGFβR kinase is the protein as identified by the NCBI sequence reference GI:195963412. In embodiments, the TGFβR kinase is the protein as identified by the NCBI sequence reference GI: 195963412, homolog or functional fragment thereof.

In embodiments, the kinase inhibitor is an Abl kinase inhibitor, a p38α MAP kinase inhibitor, a GSK-3α inhibitor, a GSK-3β inhibitor, an IP3-K inhibitor, an ALK 4 inhibitor, an ALK 5 inhibitor, a MLCK 2 inhibitor, a PIM1 kinase inhibitor, a PI3α kinase inhibitor, a ROCK-II inhibitor or a TGFβ Receptor I kinase inhibitor. In embodiments, the kinase inhibitor is an Abl kinase inhibitor, a p38α MAP kinase inhibitor, a GSK-3α inhibitor or a GSK-3β inhibitor. In embodiments, the kinase inhibitor is an Abl kinase inhibitor. In embodiments, the kinase inhibitor is a p38α MAP kinase inhibitor. In embodiments, the kinase inhibitor is a GSK-3α inhibitor. In embodiments, the kinase inhibitor is a GSK-3β inhibitor. In embodiments, the kinase inhibitor is an IP3-K inhibitor. In embodiments, the kinase inhibitor is an ALK 4 inhibitor. In embodiments, the kinase inhibitor is an ALK 5 inhibitor. In embodiments, the kinase inhibitor is a MLCK 2 inhibitor. In embodiments, the kinase inhibitor is a PIM1 kinase inhibitor. In embodiments, the kinase inhibitor is a PI3α kinase inhibitor. In embodiments, the kinase inhibitor is a ROCK-II inhibitor. In embodiments, the kinase inhibitor is a TGFβ Receptor I kinase inhibitor.

In embodiments, the kinase inhibitor has the structure of formula:

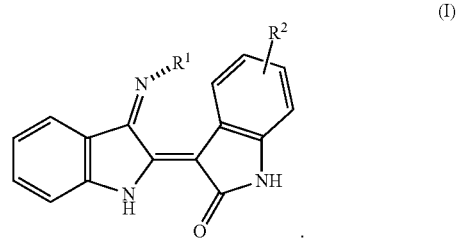

In formula (I) $R^1$ is hydrogen, $OR^3$, unsubstituted $C_1$-$C_5$ alkyl, unsubstituted heteroalkyl, unsubstituted aryl or unsubstituted heteroaryl. $R^2$ is halogen or $CF_3$. $R^3$ is hydrogen, —C(O)$R^4$, unsubstituted $C_1$-$C_5$ alkyl, unsubstituted heteroalkyl, unsubstituted aryl or unsubstituted heteroaryl. And $R^4$ is unsubstituted $C_1$-$C_5$ alkyl, unsubstituted heteroalkyl, unsubstituted aryl or unsubstituted heteroaryl.

In embodiments, $R^1$ is $OR^3$. In embodiments, $R^3$ is hydrogen or —C(O)$R^4$. In embodiments, $R^3$ is hydrogen. In embodiments, $R^3$ is —C(O)$R^4$. In further embodiments, $R^4$ is $C_1$-$C_3$ alkyl. In further embodiments, $R^4$ is methyl.

In embodiments, $R^2$ is —Br or —I. In embodiments, $R^2$ is —Br. In embodiments, $R^2$ is —I.

In some embodiments of formula (I), $R^1$ is $OR^3$, wherein $R^3$ is hydrogen and $R^2$ is —Br. In other embodiments of formula (I), $R^1$ is $OR^3$, wherein $R^3$ is —C(O)$R^4$, $R^4$ is methyl and $R^2$ is —Br. In some embodiments of formula (I), $R^1$ is $OR^3$, wherein $R^3$ is hydrogen and $R^2$ is —I. In some embodiments of formula (I), $R^1$ is $OR^3$, wherein $R^3$ is 5-membered heteroalkyl and $R^2$ is —Br. In some embodiments of formula (I), $R^1$ is $OR^3$, wherein $R^3$ is 4-membered heteroalkyl and $R^2$ is —Br.

In embodiments, the kinase inhibitor is imatinib, nilotinib,

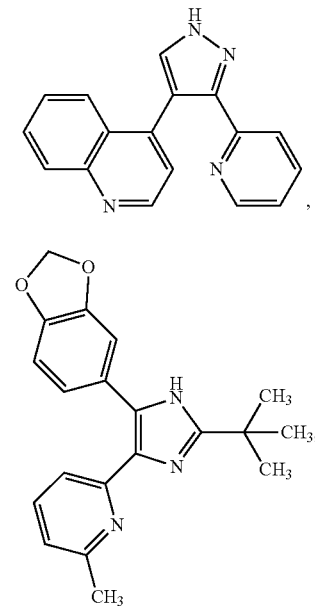

-continued
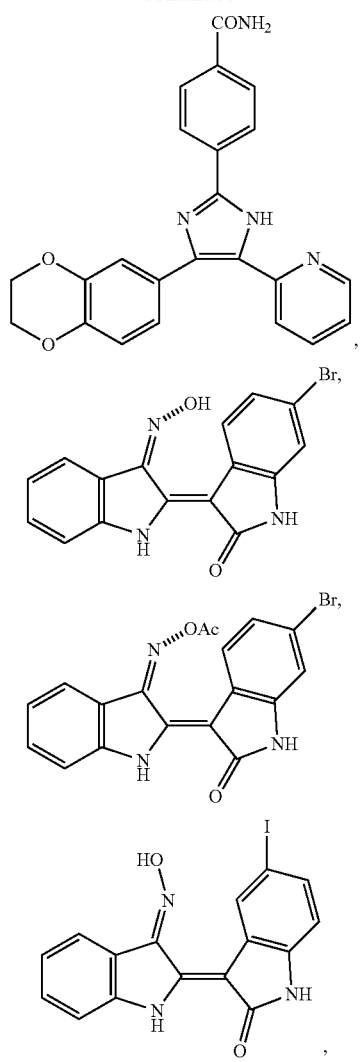
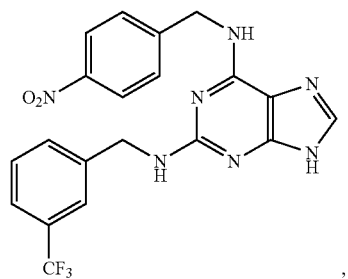
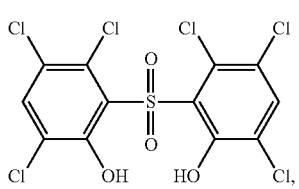
-continued
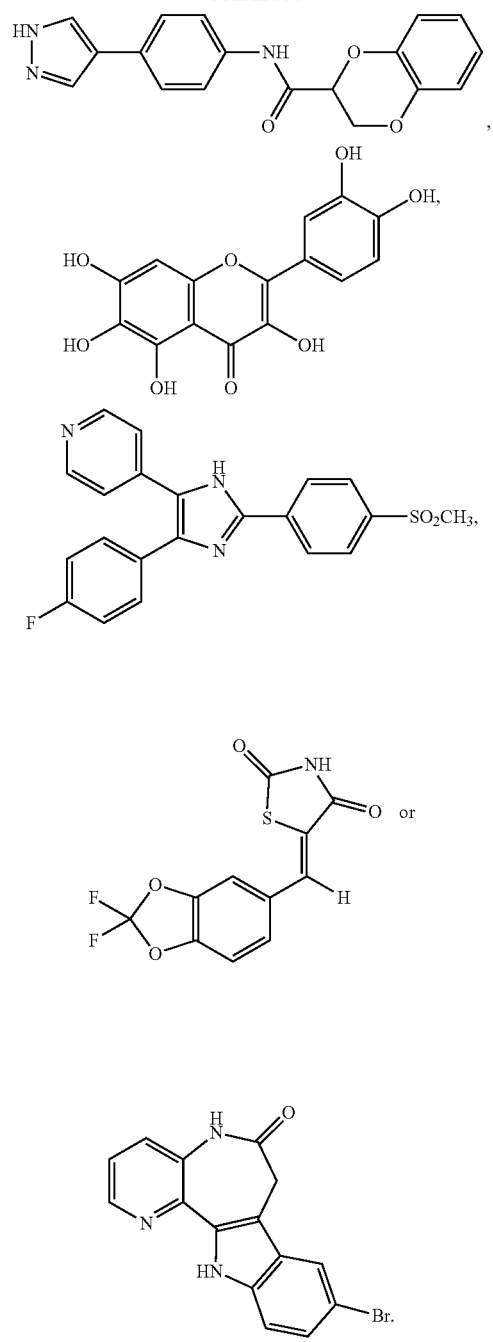
In embodiments, the kinase inhibitor has the structure of formula
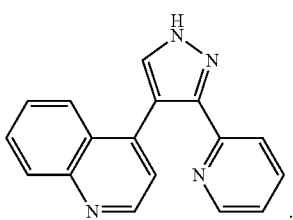 [SMILES: c1ccc(-c2n[nH]cc2-c2ccnc3ccccc23)nc1 ; "."]

In embodiments, the kinase inhibitor has the structure of formula

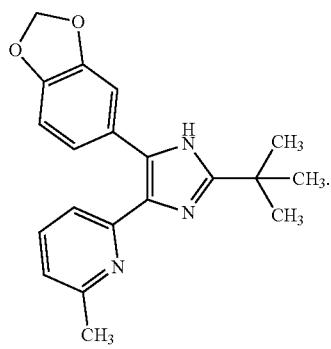 [SMILES: Cc1cccc(-c2nc(C(C)(C)C)[nH]c2-c2ccc3c(c2)OCO3)n1]

In embodiments, the kinase inhibitor has the structure of formula

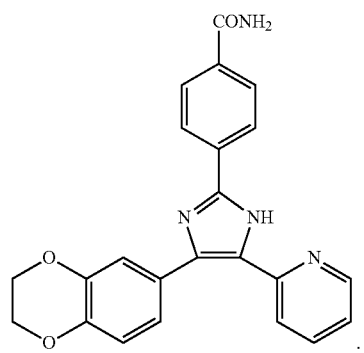 [SMILES: NC(=O)c1ccc(-c2nc(-c3ccc4c(c3)OCCO4)c(-c3ccccn3)[nH]2)cc1 ; "."]

In embodiments, the kinase inhibitor has the structure of formula

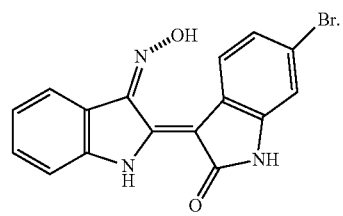

In embodiments, the kinase inhibitor has the structure of formula

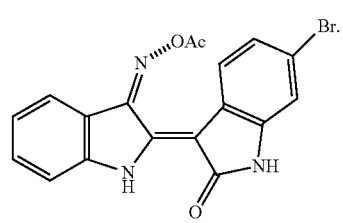

In embodiments, the kinase inhibitor has the structure of formula

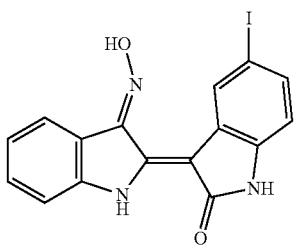

In embodiments, the kinase inhibitor has the structure of formula

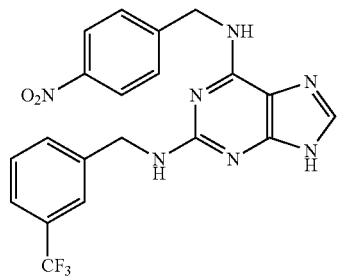

In embodiments, the kinase inhibitor has the structure of formula

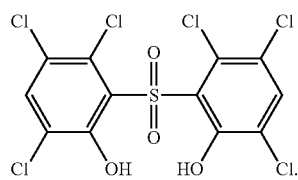 [SMILES: O=S(=O)(c1c(O)c(Cl)cc(Cl)c1Cl)c1c(O)c(Cl)cc(Cl)c1Cl]

In embodiments, the kinase inhibitor has the structure of formula.

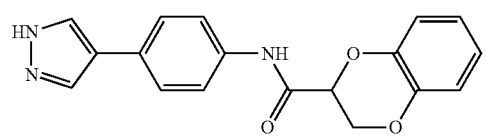

In embodiments, the kinase inhibitor has the structure of formula

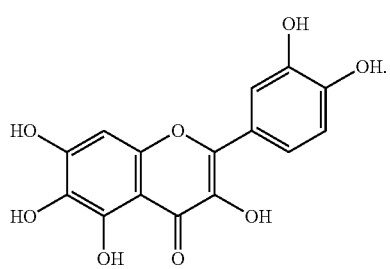 [SMILES: O=c1c(O)c(-c2ccc(O)c(O)c2)oc2cc(O)c(O)c(O)c12]

In embodiments, the kinase inhibitor has the structure of formula

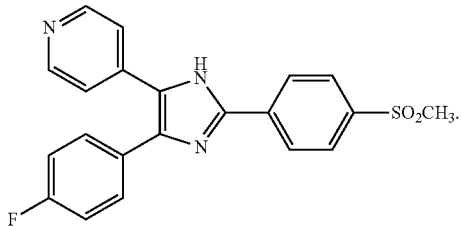 [SMILES: CS(=O)(=O)c1ccc(-c2nc(-c3ccc(F)cc3)c(-c3ccncc3)[nH]2)cc1]

In embodiments, the kinase inhibitor has the structure of formula

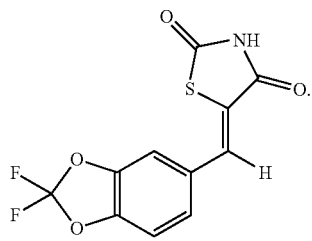 [SMILES: O=C1NC(=O)/C(=C/c2ccc3c(c2)OC(F)(F)O3)S1]

In embodiments, the kinase inhibitor has the structure of formula

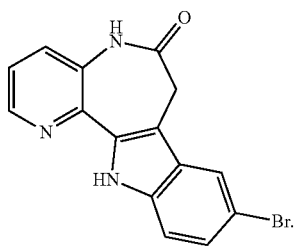 [SMILES: O=C1Cc2c([nH]c3ccc(Br)cc23)-c2ncccc2N1]

In embodiments, the kinase inhibitor is

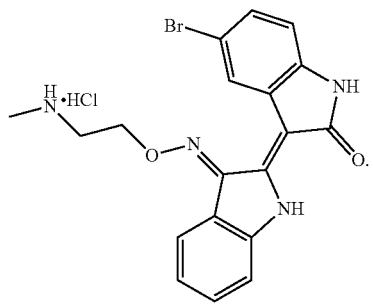 [SMILES: CNCCO/N=C1/C(=C2/C(=O)Nc3ccc(Br)cc32)Nc2ccccc21 ; Cl]

In embodiments, the kinase inhibitor is

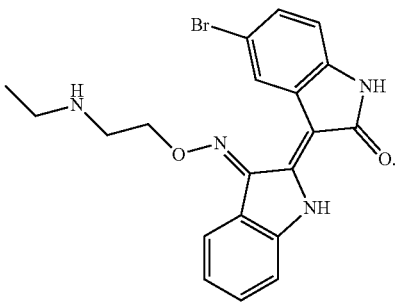 [SMILES: CCNCCO/N=C1/C(=C2/C(=O)Nc3ccc(Br)cc32)Nc2ccccc21]

In embodiments, the kinase inhibitor is imatinib. "Imatinib" as provided herein refers to 4-[(4-methylpiperazin-1-yl)methyl]-N-(4-methyl-3-{[4-(pyridin-3-yl)pyrimidin-2-yl]amino}phenyl)benzamide, and in the customary sense, refers to CAS Registry No. 152459-95-5. In embodiments, the kinase inhibitor is nilotinib. "Nilotinib" as provided herein refers to 4-methyl-N-[3-(4-methyl-1H-imidazol-1-yl)-5-(trifluoromethyl)phenyl]-3-[(4-pyridin-3-ylpyrimidin-2-yl) amino]benzamide, and in the customary sense, refers to CAS Registry No. 641571-10-0. In embodiments, the kinase inhibitor is a compound as disclosed in U.S. Pat. Nos. 5,521,184, 6,894,051, 6,958,335, 7,544,799, 7,169,791, 8,163,904, 8,293,756, 8,389,537 or 8,415,363, all of which are hereby incorporated by reference and for all purposes.

The methods provided herein are useful for delivering a nucleic acid to a cell. In embodiments, the cell forms part of an organ. In embodiments, the cell forms part of a tissue. In embodiments, the cell forms part of an organism. In embodiments, the cell forms part of an in vitro culture. In embodiments, the cell is a cancer cell. In embodiments, the cancer cell forms part of a tumor. A "tumor" as referred to herein is an abnormal mass of tissue, which can be benign (not cancerous), pre-malignant (pre-cancerous), or malignant (cancerous). In embodiments, the cell forms part of a tumor spheroid. A "tumor spheroid" as referred to herein is a three dimensional multicellular in vitro cell aggregate, which closely resembles small avascular tumors and micrometastases. Tumor spheroid aggregates are useful tools as an intermediate between monolayer culture and in vivo studies for the screening of small-molecule drugs.

In embodiments, the cell is a cancer cell and the nucleic acid is an anti-cancer nucleic acid. An "anti-cancer nucleic acid" is used in accordance with its plain ordinary meaning and refers to a nucleic acid having antineoplastic properties or the ability to inhibit the growth or proliferation of cells. In embodiments, an anti-cancer nucleic acid is a chemotherapeutic. In embodiments, an anti-cancer nucleic acid is nucleic acid identified herein having utility in methods of treating cancer. In embodiments, the nucleic acid is an antisense nucleic acid. In embodiments, the nucleic acid is an siRNA, a miRNA, a shRNA, an aptamer, a DNA or a morpholino oligonucleotide. In embodiments, the nucleic acid is an siRNA. In embodiments, the nucleic acid is a miRNA. In embodiments, the nucleic acid includes an anti-mir21 nucleic acid sequence. In embodiments, the nucleic acid includes the sequence of SEQ ID NO:1. In embodiments, the anti-mir21 nucleic acid sequence includes the sequence of SEQ ID NO:1. In embodiments, the anti-mir21 nucleic acid sequence has the sequence of SEQ ID NO:1. In embodiments, the anti-mir21 nucleic acid sequence has a sequence identity of at least 90% to SEQ ID NO:1. In embodiments, the anti-mir21 nucleic acid sequence has a sequence identity of at least 80% to SEQ ID NO:1. In embodiments, the anti-mir21 nucleic acid sequence has a sequence identity of at least 70% to SEQ ID NO:1. In embodiments, the anti-mir21 nucleic acid sequence has a sequence identity of at least 60% to SEQ ID NO:1. In embodiments, the anti-mir21 nucleic acid sequence is complementary to SEQ ID NO:2. In embodiments, the anti-mir21 nucleic acid sequence is complementary to a sequence including SEQ ID NO:2. In embodiments, the anti-mir21 nucleic acid sequence is at least 90% complementary to SEQ ID NO:2. In embodiments, the anti-mir21 nucleic acid sequence is at least 80% complementary to SEQ ID NO:2. In embodiments, the anti-mir21 nucleic acid sequence is at least 70% complementary to SEQ ID NO:2. In embodiments, the anti-mir21 nucleic acid sequence is at least 60% complementary to SEQ ID NO:2. In embodiments, the nucleic acid is an shRNA. In embodiments, the nucleic acid is an aptamer. In embodiments, the nucleic acid is a DNA. In embodiments, the nucleic acid is a morpholino oligonucleotide.

In embodiments, the nucleic acid is a single stranded antisense nucleic acid. In embodiments, the nucleic acid is a Bcl2-antisense nucleic acid. In embodiments, the nucleic acid is an androgen receptor (AR)-antisense nucleic acid.

"Bcl-2" as referred to herein includes any of the B-cell lymphoma 2 (Bcl-2) protein naturally occurring forms, homologs or variants that maintain the activity of Bcl-2 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, Bcl-2 is the protein as identified by the NCBI sequence reference GI:72198189. In embodiments, Bcl-2 is the protein as identified by the NCBI sequence reference GI:72198189, homolog or functional fragment thereof. In embodiments, Bcl-2 is the protein encoded by the nucleic acid identified by the NCBI sequence reference GI:72198188.

The term "androgen receptor" or "AR" as referred to herein includes any of the androgen receptor (AR) protein naturally occurring forms, homologs or variants (e.g., AR splice variant-7) that maintain the activity of AR (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, AR is the protein as identified by the NCBI sequence reference GI:21322252. In embodiments, AR is the protein as identified by the NCBI sequence reference GI:21322252, homolog or functional fragment thereof. In embodiments, AR is the protein encoded by the nucleic acid identified by the NCBI sequence reference GI:349501065.

In embodiments, the nucleic acid is an antisense RNA. In embodiments, the nucleic acid includes an anti-Bcl2 nucleic acid sequence. The term "anti-Bcl-2 nucleic acid sequence" as referred to herein includes any sequence capable of inhibiting Bcl-2 activity. In embodiments, the nucleic acid includes the sequence of SEQ ID NO:3. In embodiments, the anti-Bcl-2 nucleic acid sequence includes the sequence of SEQ ID NO:3. In embodiments, the anti-Bcl-2 nucleic acid sequence includes modified nucleotides. In embodiments, the anti-Bcl-2 nucleic acid sequence has the sequence of SEQ ID NO:3. In embodiments, the anti-Bcl-2 nucleic acid sequence has a sequence identity of at least 90% to SEQ ID NO:3. In embodiments, the anti-Bcl-2 nucleic acid sequence has a sequence identity of at least 80% to SEQ ID NO:3. In embodiments, the anti-Bcl-2 nucleic acid sequence has a sequence identity of at least 70% to SEQ ID NO:3. In embodiments, the anti-Bcl-2 nucleic acid sequence has a sequence identity of at least 60% to SEQ ID NO:3. In embodiments, the nucleic acid includes the sequence of SEQ ID NO:5. In embodiments, the anti-Bcl-2 nucleic acid sequence includes the sequence of SEQ ID NO:5. In embodiments, the anti-Bcl-2 nucleic acid sequence has the sequence of SEQ ID NO:5. In embodiments, the anti-Bcl-2 nucleic acid sequence has a sequence identity of at least 90% to SEQ ID NO:5. In embodiments, the anti-Bcl-2 nucleic acid sequence has a sequence identity of at least 80% to SEQ ID NO:5. In embodiments, the anti-Bcl-2 nucleic acid sequence has a sequence identity of at least 70% to SEQ ID NO:5. In embodiments, the anti-Bcl-2 nucleic acid sequence has a sequence identity of at least 60% to SEQ ID NO:5.

In embodiments, the nucleic acid includes an anti-AR nucleic acid sequence. The term "anti-AR nucleic acid sequence" as referred to herein includes any sequence capable of inhibiting AR activity. In embodiments, the nucleic acid includes the sequence of SEQ ID NO:4. In embodiments, the anti-AR nucleic acid sequence includes the sequence of SEQ ID NO:4. In embodiments, the anti-AR nucleic acid sequence includes modified nucleotides. In embodiments, the anti-AR nucleic acid sequence has the sequence of SEQ ID NO:4. In embodiments, the anti-AR nucleic acid sequence has a sequence identity of at least 90% to SEQ ID NO:4. In embodiments, the anti-AR nucleic acid sequence has a sequence identity of at least 80% to SEQ ID NO:4. In embodiments, the anti-AR nucleic acid sequence has a sequence identity of at least 70% to SEQ ID NO:4. In embodiments, the anti-AR nucleic acid sequence has a sequence identity of at least 60% to SEQ ID NO:4.

In the methods provided herein including embodiments thereof, a cell (e.g., a cancer cell) is contacted with a nucleic acid (e.g., a miRNA) and a kinase inhibitor (e.g., imatinib). In embodiments, the cancer cell is contacted with a nucleic acid and a kinase inhibitor at the same time. The methods provided herein may also include pretreating (contacting) a cancer cell with a nucleic acid without a kinase inhibitor being present, thereby forming a pretreated cancer cell. The pretreated cancer cell is subsequently treated (contacted) with the nucleic acid and a kinase inhibitor, thereby allowing the nucleic acid to enter the cell. Thus, in one embodiment, the contacting includes a first step of contacting and second step of contacting. In a further embodiment, the first step includes contacting the cancer cell with a nucleic acid and the second step includes contacting the cancer cell with a kinase inhibitor. In another further embodiment, the first step includes contacting the cancer cell with a nucleic acid and the second step includes contacting the cancer cell with a nucleic acid and a kinase inhibitor. In embodiments, the nucleic acid of the first step of contacting is identical to the nucleic acid of the second step of contacting.

Pharmaceutical Formulations

The pharmaceutical compositions provided herein include a pharmaceutically acceptable excipient, a therapeutic nucleic acid and a kinase inhibitor. The therapeutic nucleic acid is present in a therapeutically effective amount, i.e., in an amount effective to achieve its intended purpose. The actual amount effective for a therapeutic application will depend, inter alia, on the condition being treated. When administered in methods to treat a disease, the pharmaceutical compositions will contain an amount of active ingredient effective to achieve the desired result, e.g., modulating the activity of a target molecule, and/or reducing, eliminating, or slowing the progression of disease symptoms. Determination of a therapeutically effective amount of a therapeutic nucleic acid provided herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

For any composition (e.g., the therapeutic nucleic acid provided, the kinase inhibitor provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

In another aspect, a pharmaceutical formulation is provided. The pharmaceutical formulation includes a pharmaceutically acceptable excipient, a therapeutic nucleic acid and a kinase inhibitor selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor. In embodiments, the kinase inhibitor is an Abl kinase inhibitor, a p38α MAP kinase inhibitor, a GSK-3α inhibitor, a GSK-3β inhibitor, an IP3-K inhibitor, an ALK 4 inhibitor, an ALK 5 inhibitor, a MLCK 2 inhibitor, a PIM1 kinase inhibitor, a PI3α kinase inhibitor, a ROCK-II inhibitor or a TGFβ Receptor I kinase inhibitor. In embodiments, the kinase inhibitor is an Abl kinase inhibitor, a p38α MAP kinase inhibitor, a GSK-3α inhibitor or a GSK-3β inhibitor.

In embodiments, the kinase inhibitor has the structure of formula:

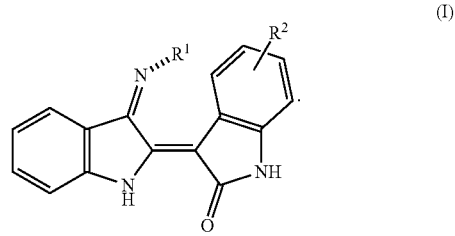

(I)

In formula (I), $R^1$ is hydrogen, $OR^3$, unsubstituted $C_1$-$C_5$ alkyl, unsubstituted heteroalkyl, unsubstituted aryl or unsubstituted heteroaryl. $R^2$ is halogen or $CF_3$. $R^3$ is hydrogen, —$C(O)R^4$, unsubstituted $C_1$-$C_5$ alkyl, unsubstituted heteroalkyl, unsubstituted aryl or unsubstituted heteroaryl. And $R^4$ is unsubstituted $C_1$-$C_5$ alkyl, unsubstituted heteroalkyl, unsubstituted aryl or unsubstituted heteroaryl.

In embodiments, $R^1$ is $OR^3$. In embodiments, $R^3$ is hydrogen or —$C(O)R^4$. In embodiments, $R^3$ is hydrogen. In embodiments, $R^3$ is —$C(O)R^4$. In further embodiments, $R^4$ is $C_1$-$C_3$ alkyl. In further embodiments, $R^4$ is methyl.

In embodiments, $R^2$ is —Br or —I. In embodiments, $R^2$ is —Br. In embodiments, $R^2$ is —I.

In some embodiments of formula (I), $R^1$ is $OR^3$, wherein $R^3$ is hydrogen and $R^2$ is —Br. In other embodiments of formula (I), $R^1$ is $OR^3$, wherein $R^3$ is —$C(O)R^4$, $R^4$ is methyl and $R^2$ is —Br. In some embodiments of formula (I), $R^1$ is $OR^3$, wherein $R^3$ is hydrogen and $R^2$ is —I. In some embodiments of formula (I), $R^1$ is $OR^3$, wherein $R^3$ is 5-membered heteroalkyl and $R^2$ is —Br. In some embodiments of formula (I), $R^1$ is $OR^3$, wherein $R^3$ is 4-membered heteroalkyl and $R^2$ is —Br.

In embodiments, the kinase inhibitor is imatinib, nilotinib,

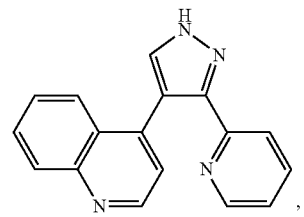

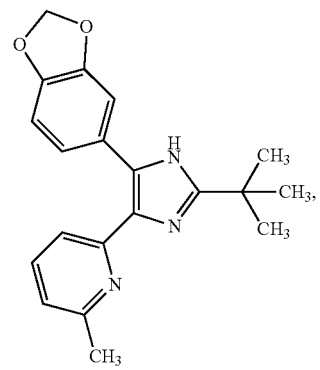

-continued
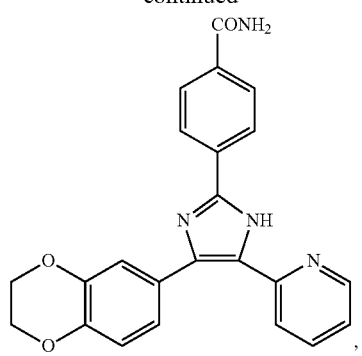
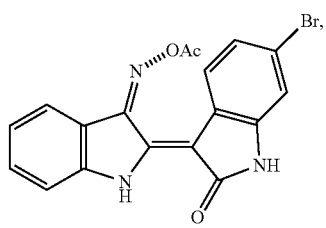
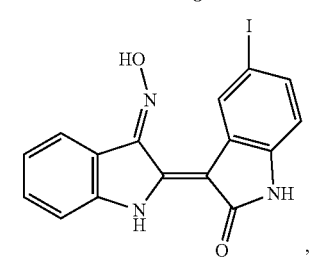
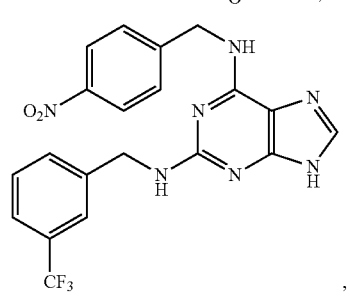
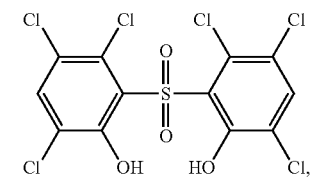
-continued
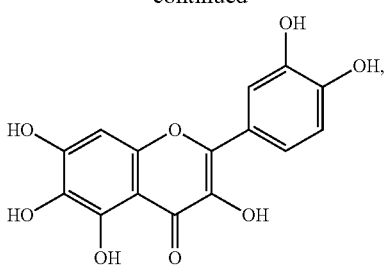
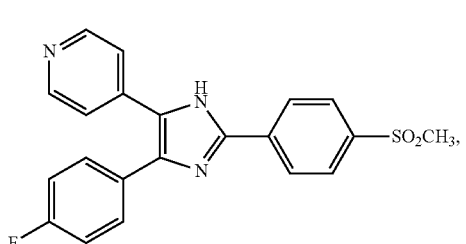
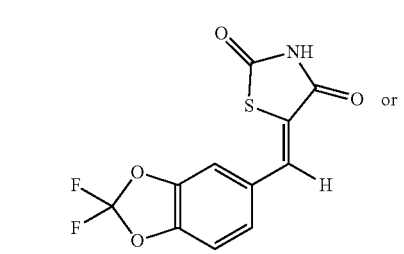
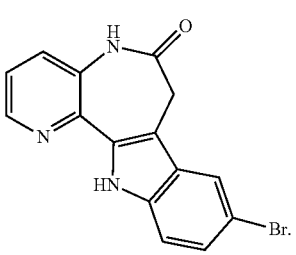
In embodiments, the kinase inhibitor is
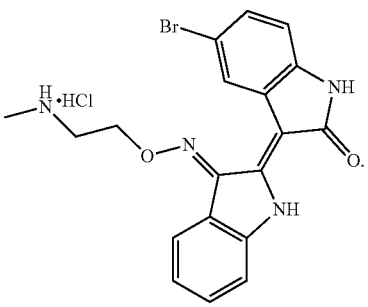 [SMILES: CNCCO/N=C1/C(=C2/C(=O)Nc3ccc(Br)cc32)Nc2ccccc21 ; Cl]

In embodiments, the kinase inhibitor is

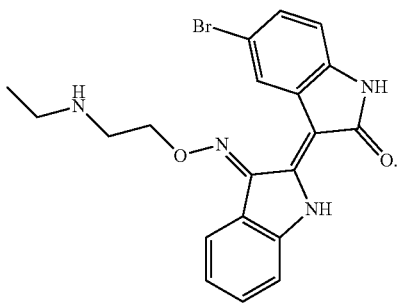 [SMILES: CCNCCO/N=C1/C(=C2/C(=O)Nc3ccc(Br)cc32)Nc2ccccc21]

In embodiments, the kinase inhibitor is a compound as disclosed in U.S. Pat. Nos. 5,521,184, 6,894,051, 6,958,335, 7,544,799, 7,169,791, 8,163,904, 8,293,756, 8,389,537 or 8,415,363, all of which are hereby incorporated by reference and for all purposes.

In embodiments, the nucleic acid is an anti-cancer nucleic acid. In embodiments, an anti-cancer nucleic acid is a chemotherapeutic. In embodiments, an anti-cancer nucleic acid is nucleic acid identified herein having utility in methods of treating cancer. In embodiments, the nucleic acid is an antisense nucleic acid. In embodiments, the nucleic acid is an siRNA, a miRNA, a shRNA, an aptamer, a DNA or a morpholino oligonucleotide. In embodiments, the nucleic acid is an siRNA. In embodiments, the nucleic acid is a miRNA. In embodiments, the nucleic acid includes an anti-mir21 nucleic acid sequence. In embodiments, the anti-mir21 nucleic acid sequence has the sequence of SEQ ID NO:1. In embodiments, the anti-mir21 nucleic acid sequence has a sequence identity of at least 90% to SEQ ID NO:1. In embodiments, the anti-mir21 nucleic acid sequence has a sequence identity of at least 80% to SEQ ID NO:1. In embodiments, the anti-mir21 nucleic acid sequence has a sequence identity of at least 70% to SEQ ID NO:1. In embodiments, the anti-mir21 nucleic acid sequence has a sequence identity of at least 60% to SEQ ID NO:1. In embodiments, the anti-mir21 nucleic acid sequence is complementary to SEQ ID NO:2. In embodiments, the anti-mir21 nucleic acid sequence is at least 90% complementary to SEQ ID NO:2. In embodiments, the anti-mir21 nucleic acid sequence is at least 80% complementary to SEQ ID NO:2. In embodiments, the anti-mir21 nucleic acid sequence is at least 70% complementary to SEQ ID NO:2. In embodiments, the anti-mir21 nucleic acid sequence is at least 60% complementary to SEQ ID NO:2. In embodiments, the nucleic acid is an shRNA. In embodiments, the nucleic acid is an aptamer. In embodiments, the nucleic acid is a DNA. In embodiments, the nucleic acid is a morpholino oligonucleotide.

Methods of Treatment

As described above, the nucleic acid of the methods provided may be an anti-cancer cell and the cell the nucleic acid is delivered to may be a cancer cell. Thus, the methods and compositions provided herein are, inter alia, useful for the treatment of cancer.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) would be known or may be determined by a person of ordinary skill in the art.

Where combination treatments are contemplated, it is not intended that the agents (i.e. anti-cancer nucleic acid, kinase inhibitor) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In one aspect, a method of treating cancer in a subject in need thereof is provided. The method includes administering to the subject an anti-cancer nucleic acid and a kinase inhibitor in a combined effective amount. The kinase inhibitor is selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor. In embodiments, the kinase inhibitor is an Abl kinase inhibitor, a p38α MAP kinase inhibitor, a GSK-3α inhibitor, a GSK-3β inhibitor, an IP3-K inhibitor, an ALK 4 inhibitor, an ALK 5 inhibitor, a MLCK 2 inhibitor, a PIM1 kinase inhibitor, a PI3α kinase inhibitor, a ROCK-II inhibitor or a TGFβ Receptor I kinase inhibitor. In embodiments, the kinase inhibitor is an Abl kinase inhibitor, a p38α MAP kinase inhibitor, a GSK-3α inhibitor or a GSK-3β inhibitor.

In embodiments, the kinase inhibitor has the structure of formula:

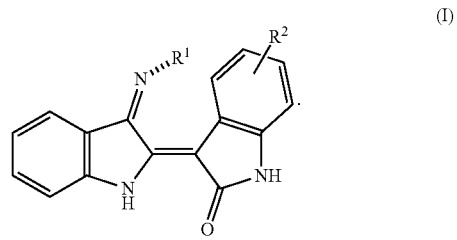

(I)

In formula (I), $R^1$ is hydrogen, $OR^3$, unsubstituted $C_1$-$C_5$ alkyl, unsubstituted heteroalkyl, unsubstituted aryl or unsubstituted heteroaryl. $R^2$ is halogen or $CF_3$. $R^3$ is hydrogen, —C(O)$R^4$, unsubstituted $C_1$-$C_5$ alkyl, unsubstituted heteroalkyl, unsubstituted aryl or unsubstituted heteroaryl. And $R^4$ is unsubstituted $C_1$-$C_5$ alkyl, unsubstituted heteroalkyl, unsubstituted aryl or unsubstituted heteroaryl.

In embodiments, $R^1$ is $OR^3$. In embodiments, $R^3$ is hydrogen or —C(O)$R^4$. In embodiments, $R^3$ is hydrogen. In embodiments, $R^3$ is —C(O)$R^4$. In further embodiments, $R^4$ is $C_1$-$C_3$ alkyl. In further embodiments, $R^4$ is methyl.

In embodiments, $R^2$ is —Br or —I. In embodiments, $R^2$ is —Br. In embodiments, $R^2$ is —I.

In some embodiments of formula (I), $R^1$ is $OR^3$, wherein $R^3$ is hydrogen and $R^2$ is —Br. In other embodiments of formula (I), $R^1$ is $OR^3$, wherein $R^3$ is —C(O)$R^4$, $R^4$ is methyl and $R^2$ is —Br. In some embodiments of formula (I), $R^1$ is $OR^3$, wherein $R^3$ is hydrogen and $R^2$ is —I. In some embodiments of formula (I), $R^1$ is $OR^3$, wherein $R^3$ is 5-membered heteroalkyl and $R^2$ is —Br. In some embodiments of formula (I), $R^1$ is $OR^3$, wherein $R^3$ is 4-membered heteroalkyl and $R^2$ is —Br.
In embodiments, the kinase inhibitor is imatinib, nilotinib,
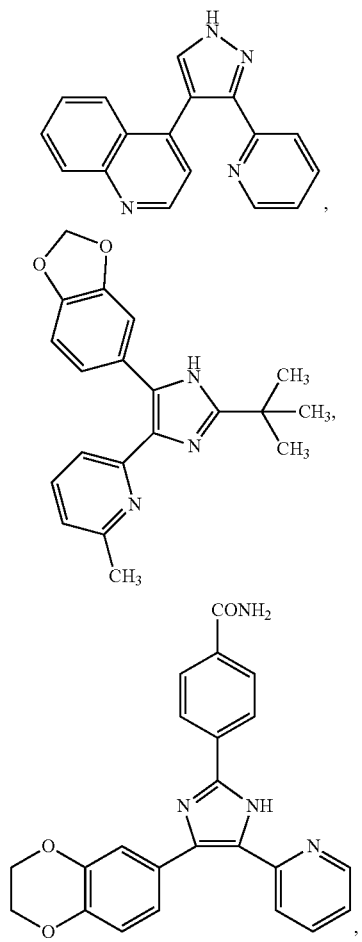
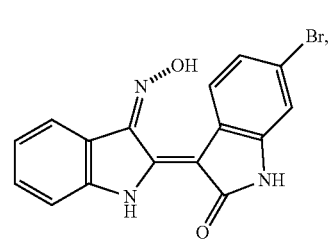
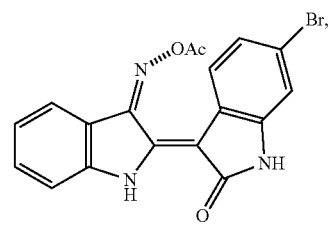
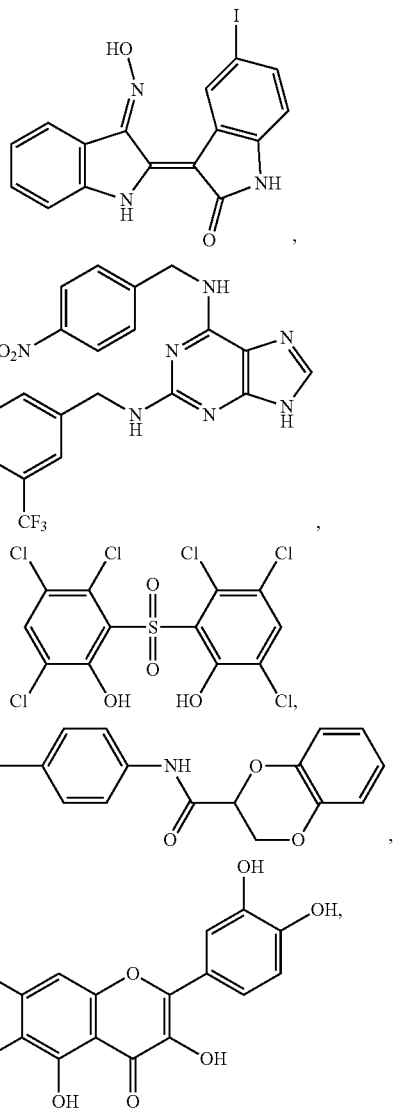
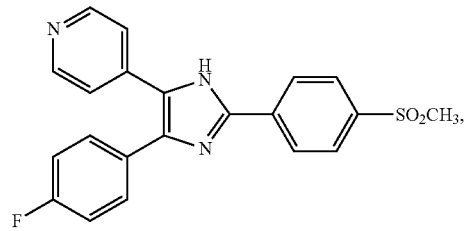
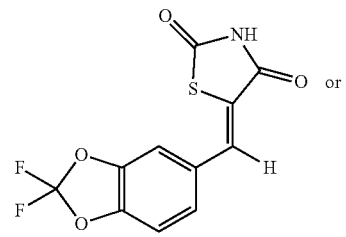

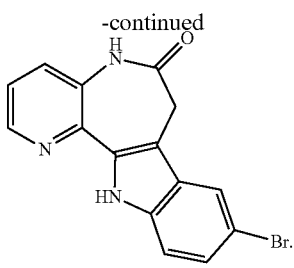

In embodiments, the kinase inhibitor is

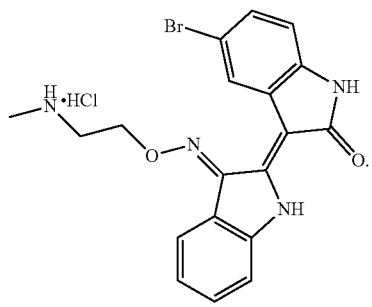 [SMILES: CNCCO/N=C1/C(=C2/C(=O)Nc3ccc(Br)cc32)Nc2ccccc21 ; Cl]

In embodiments, the kinase inhibitor is

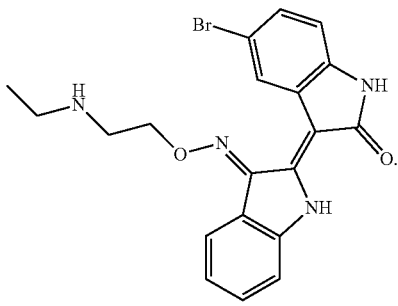 [SMILES: CCNCCO/N=C1/C(=C2/C(=O)Nc3ccc(Br)cc32)Nc2ccccc21]

In embodiments, the kinase inhibitor is a compound as disclosed in U.S. Pat. Nos. 5,521,184, 6,894,051, 6,958,335, 7,544,799, 7,169,791, 8,163,904, 8,293,756, 8,389,537 or 8,415,363, all of which are hereby incorporated by reference and for all purposes.

In embodiments, the nucleic acid is an anti-cancer nucleic acid. In embodiments, an anti-cancer nucleic acid is a chemotherapeutic. In embodiments, an anti-cancer nucleic acid is nucleic acid identified herein having utility in methods of treating cancer. In embodiments, the nucleic acid is an antisense nucleic acid. In embodiments, the nucleic acid is an siRNA, a miRNA, a shRNA, an aptamer, a DNA or a morpholino oligonucleotide. In embodiments, the nucleic acid is an siRNA. In embodiments, the nucleic acid is a miRNA. In embodiments, the nucleic acid includes an anti-mir21 nucleic acid sequence. In embodiments, the anti-mir21 nucleic acid sequence has the sequence of SEQ ID NO:1. In embodiments, the anti-mir21 nucleic acid sequence has a sequence identity of at least 90% to SEQ ID NO:1. In embodiments, the anti-mir21 nucleic acid sequence has a sequence identity of at least 80% to SEQ ID NO:1. In embodiments, the anti-mir21 nucleic acid sequence has a sequence identity of at least 70% to SEQ ID NO:1. In embodiments, the anti-mir21 nucleic acid sequence has a sequence identity of at least 60% to SEQ ID NO:1. In embodiments, the anti-mir21 nucleic acid sequence is complementary to SEQ ID NO:2. In embodiments, the anti-mir21 nucleic acid sequence is at least 90% complementary to SEQ ID NO:2. In embodiments, the anti-mir21 nucleic acid sequence is at least 80% complementary to SEQ ID NO:2. In embodiments, the anti-mir21 nucleic acid sequence is at least 70% complementary to SEQ ID NO:2. In embodiments, the anti-mir21 nucleic acid sequence is at least 60% complementary to SEQ ID NO:2. In embodiments, the nucleic acid is an shRNA. In embodiments, the nucleic acid is an aptamer. In embodiments, the nucleic acid is a DNA. In embodiments, the nucleic acid is a morpholino oligonucleotide.

EXAMPLES

Example 1

HCT-116 cells were transfected with a plasmid that expresses EGFP under the control of mir-21. When the cells express endogenous mir-21, the expression of EGFP is silenced. These cells were grown into tumor microspheroids, which were treated with an anti-mir21 mix mer oligonucleotide under gymnotic conditions (i.e., no carriers, no conjugations). When the anti-mir21 mix mer (product of Santaris Pharma, Horsholm, Denmark) enters the cells, it prevents the binding of the endogenous mir21 to its complementary sites on the 3'UTR of the EGFP gene. EGFP is then expressed and the cells glow green. Applicants discovered, by confocal microscopy, that the penetration of the anti-mir21 into the tumor microspheroid was only approximately 3 cells deep. Applicants verified this by treating the microspheroids with a Cy5-labeled anti-Bcl-2 phosphorothioate LNA gapmer. Here again, the penetration was only about 3 cell layers deep. Applicants then wanted to increase the oligo penetration and increase the amount of EGFP produced per cell. Applicants then began to screen a library of tyrosine kinase inhibitors (TKIs). These were added (100 nm-1 uM) to the media in addition to the oligo. Applicants examined 4 TKIs: Sorafenib was ineffective. However, imatinib (Gleevec, product of Novartis), dramatically increased EGFP expression in tissue culture and increased penetration of the anti-mir21 oligo in tumor microspheroids. This increased penetration was also seen with the Cy5-labeled anti-Bcl-2 oligo. In a separate experiment, nilotinib, whose mechanism of action is similar to imatinib, was also shown to have activity. This work has tremendous practical utility as it provides a way of screening for active oligos in a non-animal model, and provides a way to improve oligo penetration in tumors.

Experimental Procedures

Large Drug Screen to Identify Compounds that Facilitate ASO Cellular Uptake and Release To generate the HCT116-GFPmiR21 cell line, HCT116 cells (ATCC; human colon colorectal carcinoma cells) were grown in DMEM (Irvine Scientific, Santa Ana, Calif., USA) supplemented with 10% fetal calf serum (Irvine Scientific)+ 1 mM L-glutamine and transfected (using Lipofectamine 2000, Invitrogen) with a SapI linearized pcDNA4/ GFPmir21 plasmid DNA (Addgene). The pcDNA4/ GFPmir21 reporter plasmid expresses EGFP-N1 (Clontech), which carries a sequence with perfect complementarity to miR-21 in its 3' UTR, in the pcDNA4/TO (Invitrogen) backbone. Cells with stable plasmid integrations were selected by applying 200 μg Zeocin per ml media for 10 days. Single colonies were picked and screened for the expression of EGFP upon transfection with a 2'-O-methyl RNA complementary to miR21 relative to a control 2'O-methyl RNA complementary to miR33. EGFP reactivation is due to interference/block of the endogenous mir21 function and a consequential reactivation of EGFP mRNA translation.

The selected stable clonal cell line with the integrated EGFP (HCT116-GFPmiR21) was then mock transfected (Lip-2000) or transfected with: (i) a 2'O-Me-oligonucleotide designed to bind and block mir21 activity (called an antagomir); (ii) an irrelevant 2'O-Me-oligonucleotide to test for non-specific reactivation of EGFP; (iii) an anti-miR21 phosphorothioate (PS)-mixmer. (The oligo is called a mixmer because it contains LNA moieties at some positions, and unmodified DNA at other positions. This oligo was provided by Santaris, Horsholm, DK). The results obtained from the antagomir were compared with the EGFP reactivation obtained by gymnotic delivery of an anti-miR21 PS-mixmer. When compared to the 2'O-Me-oligonucleotide antagomir, the anti-miR21 PS-mixmer proved to be more effective in blocking miR21. Optimal conditions for EGFP reactivation were established to be i) cell seeding at 50% confluence; ii) 1 μM of anti miR21 treatment approximately 18 hrs following cell seeding. Under these conditions, EGFP reactivation could be seen for up to 30 days.

Drug screens were conducted in a 96-well plate format. Thirty to forty thousand cells/well were seeded 18-24 hrs prior oligo treatment. 1 μM final concentration of the anti-miR21 PS-mixmer was added in each well, immediately followed by the addition of the various compounds, also at a 1 μM final concentration. A minimum of 3 wells were treated per each compound and compared against the outcome produced by the oligo alone, or the compound alone, for reactivation of EGFP expression. EGFP reactivation is an indication of oligo uptake and efficacy in blocking endogenous miR21 activity; and it was detected with a plate reader 5-6 days after treatment.

A robotic screening of a library of tyrosine kinase inhibitors (TKIs) was performed. Out of approximately 250 drugs already tested, approximately 14 have demonstrated potent effects on the facilitation of ASO uptake and function. These compounds are under investigation with the aim of determining the mechanism and the lowest concentration required for maximal enhancement of ASO function. For the 14 compounds identified as active in the initial screen, EGFP reactivation was monitored every day for up to 6 days. To determine if any compound affected ASO intracellular release, cells were first treated with 1 μM anti-miR21 PS-mixmer. The next day the media was removed and cells were washed twice with PBS. After adding fresh media the cell were treated with 1 μM of each active compound. Since ASO uptake had already occurred, any enhancement of EGFP expression in active compound-treated cells would be an indication of improved ASO intracellular release.

The most potent compounds identified in the screen were further tested in a 3D model system by employing cultures of human tumor microspheroids. The HCT-116 EGFP-miR21 stable, clonal cell line was used to create the microspheroids in 96-well hanging-drop plates (Perfecta 3D, Biometrix Inc., Ann Arbor, Mich.). Following trypsinization, the cells were lifted and re-suspended at a density of $3 \times 10^5$ cells in 300 μL DMEM (Irvine Scientific, Santa Ana, Calif., USA) supplemented with 10% fetal calf serum (Irvine Scientific), 1 mM L-glutamine, 5% non-essential amino acids. To improve the 3D structure of the spheroids, 2.5% Matrigel™ can be added to the cell seeding solution. Forty microliters of cells in suspension were used to seed each well. Treatments with the selected drugs were performed 24-48 hours following the seeding and were based on the growth of the microspheroids. The selected microspheroid sizes ranged approximately between 100 and 250 μm at the time of treatment. In another experiment, to monitor ASO distribution in this system, Applicants used Cy5-labeled PS-ASO. (Note: EGFP protein expression is an indication of ASO uptake AND function, as in a 2D cell monolayer system. The Cy-labeled PS-ASO experiment indicates cell uptake ONLY). The Cy5-PS-ASO was added at a 1 μM concentration to the hanging microspheroid; a few minutes later the TKI was added, also at a 1 μM concentration.

All microspheroids were incubated for additional 5 days and analyzed with a Zeiss confocal microscope. Z-stack images were acquired approximately every 10 μm for each spheroid. A minimum of 4-spheroids with comparable sizes were analyzed for each ASO-compound combination and compared to treatment with compound alone or ASO alone.

TABLE 1

Kinase inhibitor activities.

| Compound | IC$_{50}$ | Activity |
|---|---|---|
| 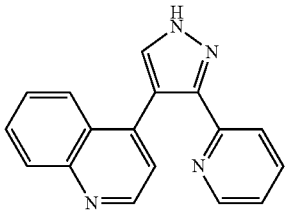 [SMILES: c1ccc(-c2n[nH]cc2-c2ccnc3ccccc23)nc1] | IC$_{50}$ = 51 nM for TGF-b Receptor I kinase.<br>IC$_{50}$ = 740 nM for p38a MAP kinase.<br>IC$_{50}$ = 89 nM for TGF-b-dependent cellular growth in NIH 3T3 mouse fibroblasts.<br>IC$_{50}$ = 47 nM for transcription activation in mink lung cells. | + |

TABLE 1-continued

Kinase inhibitor activities.

| Compound | IC$_{50}$ | Activity |
|---|---|---|
| (structure: 4-(1,3-benzodioxol-5-yl)-5-(6-methylpyridin-2-yl)-2-(propan-2-yl)-1H-imidazole hydrochloride) | IC$_{50}$ = 129 nM for activin receptor-like kinase 4.<br>IC$_{50}$ = 47 nM for activin receptor-like kinase 5.<br>IC$_{50}$ = 10.6 μM for p38 MAPKa | + |
| (structure: 4-[4-(2,3-dihydro-1,4-benzodioxin-6-yl)-5-(pyridin-2-yl)-1H-imidazol-2-yl]benzamide) | IC$_{50}$ = 500 nM for ALK5<br>IC$_{50}$ = 12 mM for p38a MAPK<br>IC$_{50}$ = 0.3 mM for CK1d<br>IC$_{50}$ = 200 nM for CK1 (S. pombe) | + |
|  | IC$_{50}$ = 5 nM for GSK-3a/b<br>IC$_{50}$ = 83 nM for Cdk5/p25<br>IC$_{50}$ = 300 nM for Cdk2/A<br>IC$_{50}$ = 320 nM for Cdk1/B | ++ |
|  | IC$_{50}$ = 10 nM for GSK-3a/b<br>IC$_{50}$ = 2.4 mM for Cdk5/p25<br>IC$_{50}$ = 4.3 mM for Cdk2/A | +++ |
| (structure: 6-iodo-3-[(3E)-3-(hydroxyimino)-1,3-dihydro-2H-indol-2-ylidene]-1,3-dihydro-2H-indol-2-one) | IC$_{50}$ = 9 nM for GSK-3b | ++ |
| (structure: N-(4-nitrobenzyl)-N'-(3-trifluoromethylbenzyl)-9H-purine-2,6-diamine) | IC$_{50}$ = 10.2 uM for IP3-K | + |

TABLE 1-continued

Kinase inhibitor activities.

| Compound | IC$_{50}$ | Activity |
|---|---|---|
| 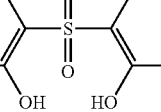 | IC$_{50}$ = 130 nM for p38a MAPK.<br>IC$_{50}$ = 550 nM and p38b MAPK | + |
| 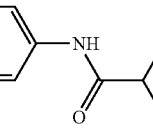 | IC$_{50}$ = 1.5 nM for ROCK-II.<br>IC$_{50}$ = 72 nM for myosin light chain 2 phosphorylation on Thr18/Ser19 in A7r5 cells. | + |
| 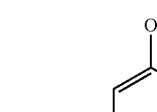 | IC$_{50}$ = 340 nM for PIM1 Kinase.<br>IC$_{50}$ = 3.45 µM for PIM2 Kinase | + |
| 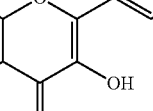 | IC$_{50}$ = 30 nM for p38 MAP kinase.<br>IC$_{50}$ = 200 nM for inhibiting IL-1 production in human monocytes | + |
| 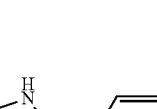 | IC$_{50}$ = 250 nM for PI3-Kγβ<br>IC$_{50}$ = 4.5 mM for PI3-Kα<br>IC$_{50}$ > 20 mM for PI3-Kα and δ | + |
| 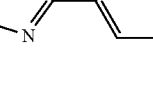 | IC$_{50}$ = 18 nM for GSK-3Beta | + |

Cells (7500/well) were seeded in 96-well plates overnight, treated with 1 uM of compounds and 1 uM of oligos for 6 days. Fluorescence intensities were measured at excitation = 495 nm and emission = 525 nm using a plate reader. Assays were done in duplicate. For a positive control, cells were treated with 5 uM or 10 uM of imatinib mesylate. Fluorescence enhancement could be detected using a microscope, but cell numbers were reduced significantly.

Example 2

The most important target in prostate cancer is the androgen receptor (AR). This protein is expressed early in the disease and continues to be expressed throughout its course, driving the growth, metastatic capability and anti-apoptotic phenotype of the prostate cancer cells. For the clinical therapy of prostate cancer, it is critical to either block the function of the wild type (full length) AR [AR-FL], or optimally, to eliminate it entirely. However, during the progression of the disease, and under the selective pressure of the drugs employed to treat patients, the AR develops mutations over time. The most common, and most lethal of these late mutations is an AR splice variant called AR-V7 (androgen receptor variant-7). In the AR-V7 mutation, the ligand binding domain, which is found in exons 5-8 of the AR pre-mRNA, is spliced out. However, the remaining exons 1-3 translocate to the nucleus in the absence of androgen, where they are constitutively active and drive tumor growth. Therefore, it is of great importance to develop a strategy to eliminate this drug-resistant target in addition to the wild type AR. Applicants have found that a TKI inhibitor (6-BIO) can downregulate both forms of the androgen receptor and that this effect is synergistic when combined with an antisense oligo targeted to the same gene (see FIG. 9 and FIG. 10). Applicants further showed that combining the drug with the antisense oligonucleotide gapmer results in a synergistic effect (FIG. 10). Similar results have been obtained with Bcl-2. (6-BIO) TKI was also shown to be synergistic when paired with a gapmer antisense oligonucleotide targeted against BCL-2.

SEQUENCE LISTING anti-mir21: SEQ ID NO: 1:
5'- tcagtctgataagcta 3' endogenous mir21: SEQ ID NO: 2:
5'- uagcuuaucagacugauguuga 3' anti-BcL-2 nucleic acid: SEQ ID NO: 3:
5'-mCsTsCsCsCsAsAsCsGsTsGsCsGsmCsmCsA-3' anti-AR nucleic acid: SEQ ID NO: 4:
5'-accaagtttcttcagc-3' anti-BcL-2 nucleic acid: SEQ ID NO: 5:
5'-CTCCCAACGTGCGCCA-3'

EMBODIMENTS

Embodiment 1

A method of delivering a nucleic acid to a cell, the method comprising: (i) contacting a cell with a nucleic acid and a kinase inhibitor selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor; and (ii) allowing said nucleic acid to enter said cell.

Embodiment 2

The method of embodiment 1, wherein said kinase inhibitor is an Abl kinase inhibitor, a p38α MAP kinase inhibitor, a GSK-3α inhibitor, a GSK-3β inhibitor, an IP3-K inhibitor, an ALK 4 inhibitor, an ALK 5 inhibitor, a MLCK 2 inhibitor, a PIM1 kinase inhibitor, a PI3α kinase inhibitor, a ROCK-II inhibitor or a TGFβ Receptor I kinase inhibitor.

Embodiment 3

The method of embodiment 1, wherein said kinase inhibitor is an Abl kinase inhibitor, a p38α MAP kinase inhibitor, a GSK-3α inhibitor or a GSK-3β inhibitor.

Embodiment 4

The method of embodiment 1, wherein said kinase inhibitor has the structure of formula:

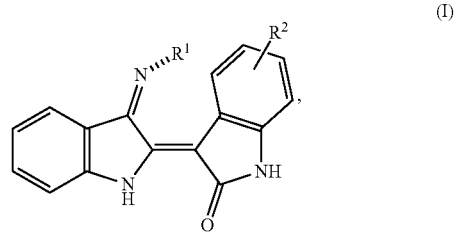

(I)

wherein $R^1$ is hydrogen, $OR^3$, unsubstituted $C_1$-$C_5$ alkyl, unsubstituted heteroalkyl, unsubstituted aryl or unsubstituted heteroaryl; $R^2$ is halogen or $CF_3$; $R^3$ is hydrogen, —$C(O)R^4$, unsubstituted $C_1$-$C_5$ alkyl, unsubstituted heteroalkyl, unsubstituted aryl or unsubstituted heteroaryl; and $R^4$ is unsubstituted $C_1$-$C_5$ alkyl, unsubstituted heteroalkyl, unsubstituted aryl or unsubstituted heteroaryl.

Embodiment 5

The method of embodiment 1, wherein said kinase inhibitor is imatinib, nilotinib,

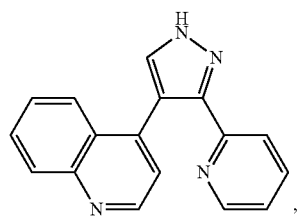

,

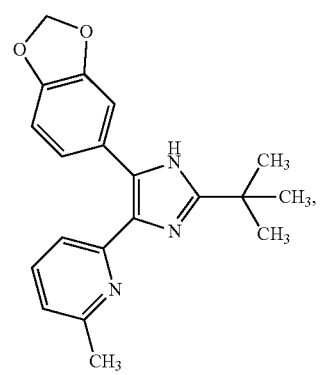

-continued

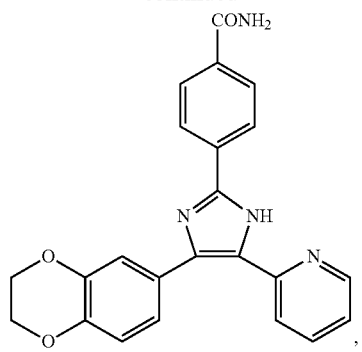
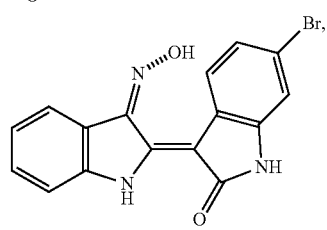
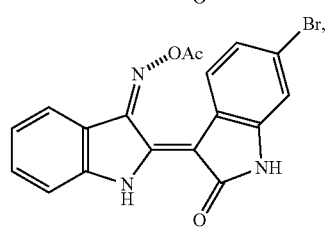
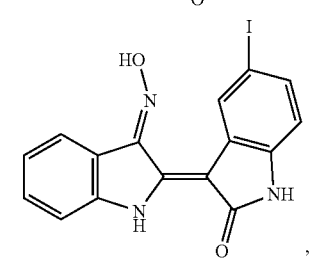
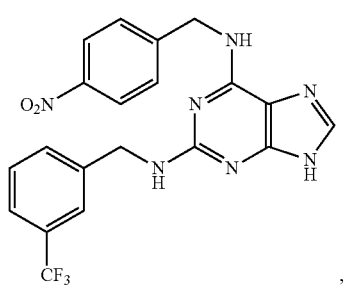
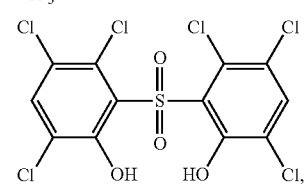
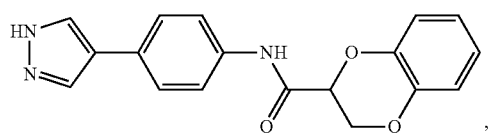

-continued

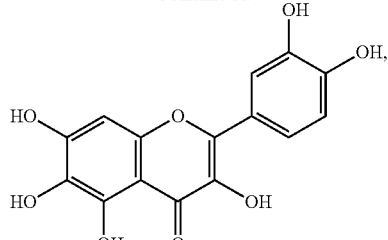
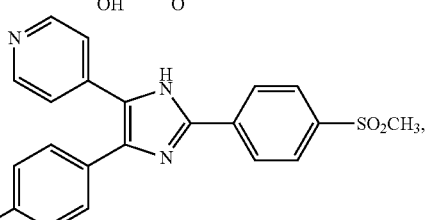
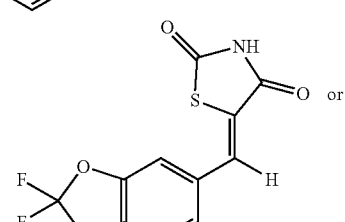
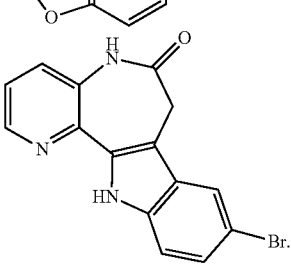

Embodiment 6

The method of one of embodiments 1 to 5, wherein said cell is a cancer cell and said nucleic acid is an anti-cancer nucleic acid.

Embodiment 7

The method of one of embodiments 1 to 6, wherein said nucleic acid is an antisense nucleic acid.

Embodiment 8

The method of one of embodiments 1 to 6, wherein said nucleic acid is an siRNA, a miRNA, a shRNA, an aptamer, a DNA or a morpholino oligonucleotide.

Embodiment 9

A pharmaceutical formulation comprising a pharmaceutically acceptable excipient, a therapeutic nucleic acid and a kinase inhibitor selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor.

Embodiment 10

The pharmaceutical composition of embodiment 9, wherein said kinase inhibitor is an Abl kinase inhibitor, a p38α MAP kinase inhibitor, a GSK-3α inhibitor, a GSK-3β inhibitor, an IP3-K inhibitor, an ALK 4 inhibitor, an ALK 5 inhibitor, a MLCK 2 inhibitor, a PIM1 kinase inhibitor, a PI3α kinase inhibitor, a ROCK-II inhibitor or a TGFβ Receptor I kinase inhibitor.

Embodiment 11

The pharmaceutical composition of embodiment 9, wherein said kinase inhibitor is an Abl kinase inhibitor, a p38α MAP kinase inhibitor, a GSK-3α inhibitor or a GSK-3β inhibitor.

Embodiment 12

The pharmaceutical composition of embodiment 9, wherein said kinase inhibitor has the structure of formula:

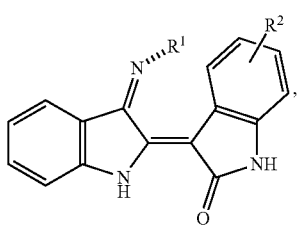

(I)

wherein $R^1$ is hydrogen, $OR^3$, unsubstituted $C_1$-$C_5$ alkyl, unsubstituted heteroalkyl, unsubstituted aryl or unsubstituted heteroaryl; $R^2$ is halogen or $CF_3$; $R^3$ is hydrogen, —C(O)$R^4$, unsubstituted $C_1$-$C_5$ alkyl, unsubstituted heteroalkyl, unsubstituted aryl or unsubstituted heteroaryl; and $R^4$ is unsubstituted $C_1$-$C_5$ alkyl, unsubstituted heteroalkyl, unsubstituted aryl or unsubstituted heteroaryl.

Embodiment 13

The pharmaceutical composition of embodiment 9, wherein said kinase inhibitor is imatinib, nilotinib,

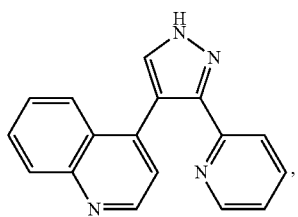

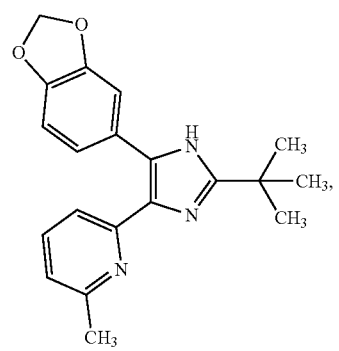

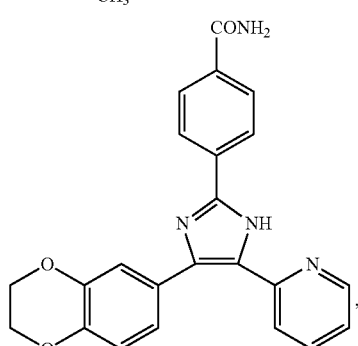

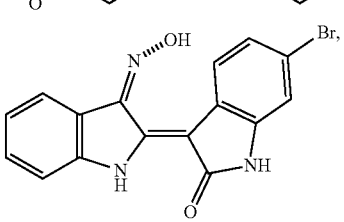

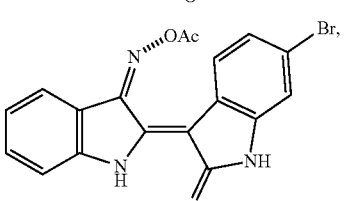

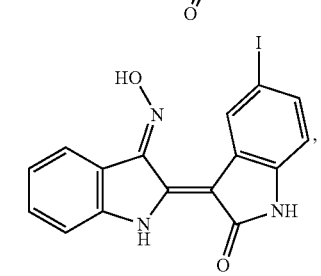

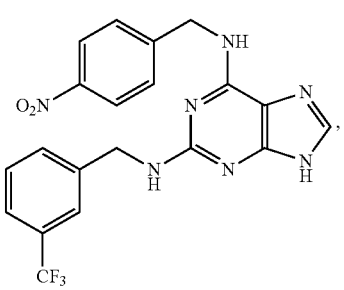

-continued

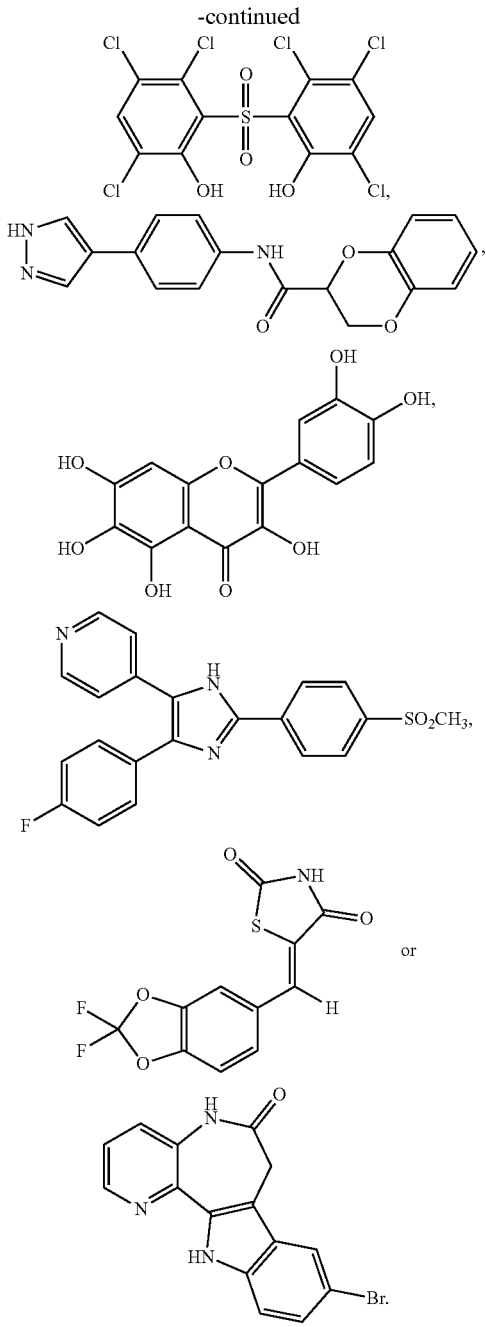

Embodiment 14

The pharmaceutical composition of one of embodiments 9 to 1313, wherein said nucleic acid is an anti-cancer nucleic acid.

Embodiment 15

The pharmaceutical composition of one of embodiments 9 to 14, wherein said nucleic acid is an antisense nucleic acid.

Embodiment 16

The pharmaceutical composition of one of embodiments 9 to 14, wherein said nucleic acid is an siRNA, a miRNA, a shRNA, an aptamer, a DNA or a morpholino oligonucleotide.

Embodiment 17

A method of treating cancer in a subject in need thereof, the method comprising administering to the subject an anti-cancer nucleic acid and a kinase inhibitor in a combined effective amount, wherein said kinase inhibitor is selected from the group consisting of an Abl kinase inhibitor, a p38 mitogen-activated protein (p38 MAP) kinase inhibitor, a glycogen synthase kinase (GSK) inhibitor, an inositol 1,4,5-trisphosphate 3 kinase (IP3-K) inhibitor, an activin receptor-like kinase (ALK) inhibitor (4 and 5), a myosin light chain kinase (MLCK) inhibitor, a proto-oncogene serine/threonine-protein 1 (PIM1) kinase inhibitor, a phosphatidylinositol-4,5-bisphosphate 3 (PI3) kinase inhibitor, a rho-associated protein kinase (ROCK) inhibitor, and a transforming growth factor beta receptor (TGFβ Receptor) kinase inhibitor.

Embodiment 18

The method of embodiment 17, wherein said kinase inhibitor is an Abl kinase inhibitor, a p38α MAP kinase inhibitor, a GSK-3α inhibitor, a GSK-3β inhibitor, an IP3-K inhibitor, an ALK 4 inhibitor, an ALK 5 inhibitor, a MLCK 2 inhibitor, a PIM1 kinase inhibitor, a PI3α kinase inhibitor, a ROCK-II inhibitor or a TGFβ Receptor I kinase inhibitor.

Embodiment 19

The method of embodiment 17, wherein said kinase inhibitor is an Abl kinase inhibitor, a p38α MAP kinase inhibitor, a GSK-3α inhibitor or a GSK-3β inhibitor.

Embodiment 20

The method of embodiment 17, wherein said kinase inhibitor has the structure of formula:

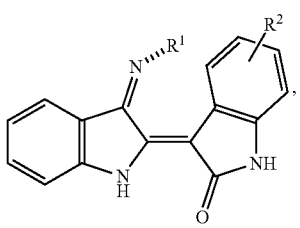

(I)

wherein $R^1$ is hydrogen, $OR^3$, unsubstituted $C_1$-$C_5$ alkyl, unsubstituted heteroalkyl, unsubstituted aryl or unsubstituted heteroaryl; $R^2$ is halogen or $CF_3$; $R^3$ is hydrogen, —C(O)$R^4$, unsubstituted $C_1$-$C_5$ alkyl, unsubstituted heteroalkyl, unsubstituted aryl or unsubstituted heteroaryl; and $R^4$ is unsubstituted $C_1$-$C_5$ alkyl, unsubstituted heteroalkyl, unsubstituted aryl or unsubstituted heteroaryl.

Embodiment 21
The method of embodiment 18, wherein said kinase inhibitor is imatinib, nilotinib,
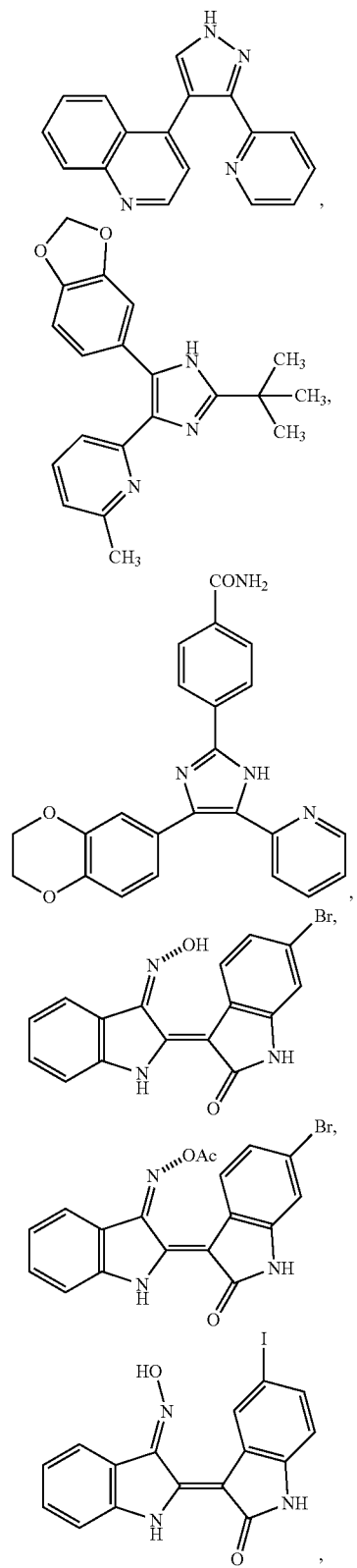
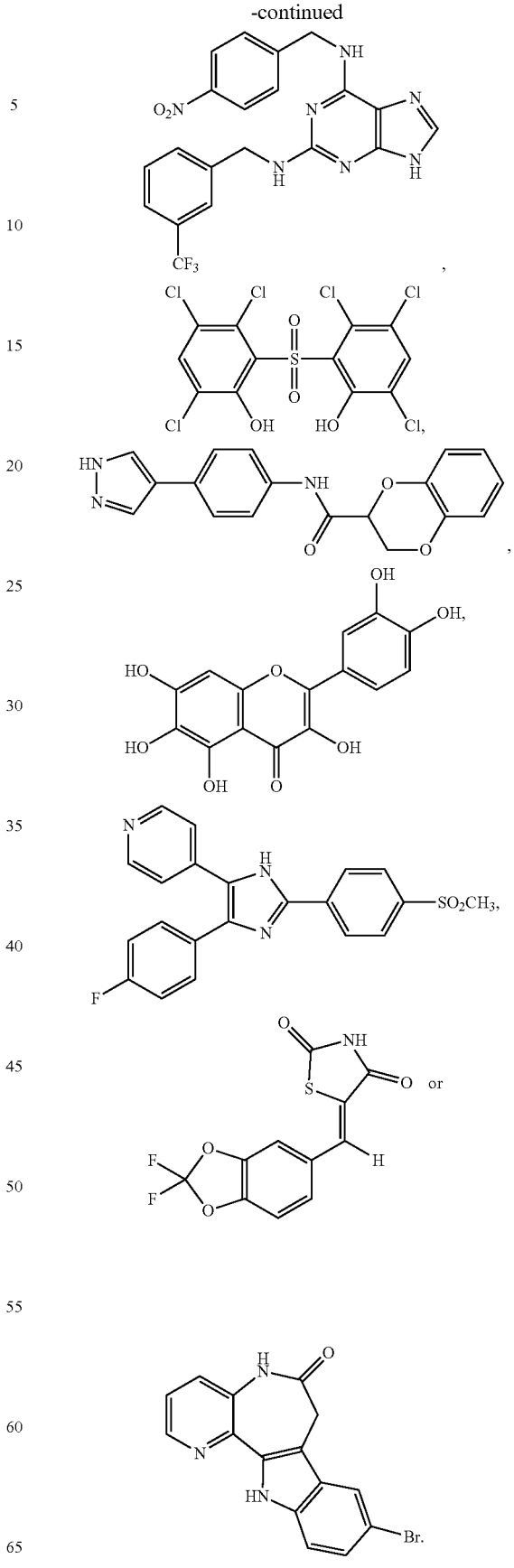

Embodiment 22

The method of one of embodiments 17 to 21, wherein said nucleic acid is an antisense nucleic acid.

Embodiment 23

The method of one of embodiments 17 to 21, wherein said nucleic acid is an siRNA, a miRNA, a shRNA, an aptamer, a DNA or a morpholino oligonucleotide.

What is claimed is:

1. A method of increasing delivery of nucleic acids to cells in vitro, the method comprising:
   (i) coadministering to said cells said nucleic acids and a combined effective amount of a kinase inhibitor, wherein said cells are non-cancerous cells; and
   (ii) allowing said nucleic acids to enter said cells, wherein the nucleic acids (a) comprise one or more nucleotide analogs or (b) are at most 50 nucleotides in length;
   wherein the combined effective amount is effective to increase delivery of said nucleic acids to said cells,
   wherein the kinase inhibitor is a glycogen synthase kinase (GSK) inhibitor and further wherein the kinase inhibitor has the structure of formula:

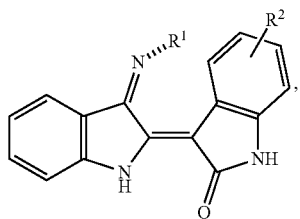

(I)

wherein $R^1$ is hydrogen, $OR^3$, unsubstituted $C_1$-$C_5$ alkyl, unsubstituted heteroalkyl, unsubstituted aryl or unsubstituted heteroaryl;
$R^2$ is halogen or $CF_3$;
$R^3$ is hydrogen, —C(O)$R^4$, unsubstituted $C_1$-$C_5$ alkyl, unsubstituted heteroalkyl, unsubstituted aryl or unsubstituted heteroaryl; and
$R^4$ is unsubstituted $C_1$-$C_5$ alkyl, unsubstituted heteroalkyl, unsubstituted aryl or unsubstituted heteroaryl.

2. The method of claim 1, wherein said kinase inhibitor is a GSK-3α inhibitor or a GSK-3β inhibitor.

3. The method of claim 1, wherein the kinase inhibitor is

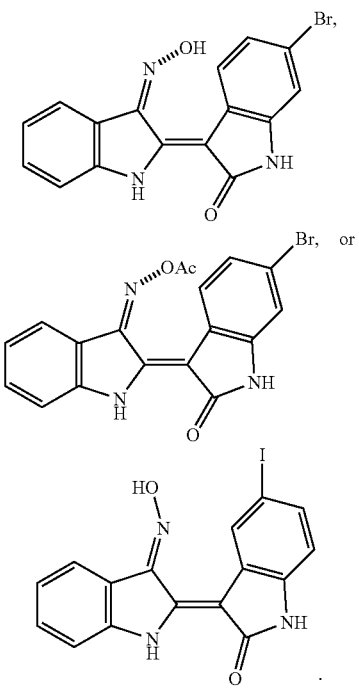

4. The method of claim 1, wherein said nucleic acids comprise antisense nucleic acids.

5. The method of claim 1, wherein said nucleic acids comprise a siRNA, a miRNA, a shRNA, an aptamer, a DNA or a morpholino oligonucleotide.

* * * * *